US006469120B1

(12) United States Patent
Elfersy et al.

(10) Patent No.: US 6,469,120 B1
(45) Date of Patent: *Oct. 22, 2002

(54) WATER-STABILIZED ORGANOSILANE COMPOUNDS AND METHODS FOR USING THE SAME

(75) Inventors: Jacques E. Elfersy, Atlanta; Joachim Berkner, Smyrna; Timothy C. Moses, Stockbridge, all of GA (US)

(73) Assignee: BioShield Technologies, Inc., Norcross, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/590,493

(22) Filed: Jun. 9, 2000

Related U.S. Application Data

(60) Continuation of application No. 09/390,008, filed on Sep. 3, 1999, now abandoned, which is a division of application No. 08/852,474, filed on May 7, 1997, now Pat. No. 5,954,869.

(51) Int. Cl.$^7$ .................... C08G 77/04; B05D 1/00
(52) U.S. Cl. .................... 528/29; 528/25; 528/38; 106/14.11; 106/287.16; 536/56; 536/84; 536/111; 536/123.1; 427/382
(58) Field of Search .................... 528/25, 27, 38; 536/56, 84, 111, 123.1; 106/14.11, 287.16; 427/387

(56) References Cited

U.S. PATENT DOCUMENTS

| | | | |
|---|---|---|---|
| 3,560,385 A | 2/1971 | Roth | |
| 3,730,701 A | 5/1973 | Isquith et al. | |
| 3,794,736 A | 2/1974 | Abbott et al. | |
| 3,814,739 A | 6/1974 | Takeda | |
| 3,817,739 A | 6/1974 | Abbott et al. | 424/78 |
| 3,860,709 A | 1/1975 | Abbott et al. | |
| 3,865,728 A | 2/1975 | Abbott et al. | 210/169 |
| 4,035,332 A | 7/1977 | Gomyo et al. | 260/33.2 SB |
| 4,110,263 A | 8/1978 | Lindermann et al. | 252/545 |
| 4,243,767 A | 1/1981 | Kaufmann et al. | 525/102 |
| 4,282,366 A | 8/1981 | Eudy | |
| 4,284,548 A | 8/1981 | Kaufmann et al. | 260/38 |
| 4,395,454 A | 7/1983 | Baldwin | 428/290 |
| 4,408,996 A | 10/1983 | Baldwin | |
| 4,414,268 A | 11/1983 | Baldwin | |
| 4,446,292 A | 5/1984 | Chang et al. | 528/29 |
| 4,465,849 A | 8/1984 | Tarae et al. | 556/450 |
| 4,467,081 A | 8/1984 | Chang et al. | 528/26 |
| 4,501,872 A | 2/1985 | Chang et al. | 528/18 |
| 4,504,541 A | 3/1985 | Yasuda et al. | |
| 4,514,342 A | 4/1985 | Billington et al. | 260/952 |
| 4,555,545 A | 11/1985 | Kimura et al. | 524/858 |
| 4,561,435 A | 12/1985 | McKnight et al. | 128/156 |
| 4,613,451 A | 9/1986 | Chang et al. | 252/182 |
| 4,615,882 A | 10/1986 | Stockel | 424/80 |
| 4,615,937 A | 10/1986 | Bouchette | |
| 4,622,369 A | 11/1986 | Chang et al. | 525/440 |
| 4,623,697 A | 11/1986 | Chang et al. | 525/61 |
| 4,631,273 A | 12/1986 | Blehm et al. | 514/29 |
| 4,631,297 A | * 12/1986 | Battice et al. | 521/78 |
| 4,648,904 A | * 3/1987 | DePasquale et al. | 106/2 |
| 4,657,941 A | 4/1987 | Blackwell et al. | 522/14 |
| 4,692,374 A | 9/1987 | Bouchette | |
| 4,736,467 A | 4/1988 | Schwartz et al. | 2/114 |
| 4,772,593 A | 9/1988 | Whalen et al. | 514/63 |
| 4,822,667 A | 4/1989 | Goad et al. | 428/265 |
| 4,842,766 A | * 6/1989 | Blehm et al. | 252/309 |
| 4,919,998 A | 4/1990 | Goad et al. | 428/265 |
| 4,921,701 A | 5/1990 | Blank | |
| 4,939,289 A | 7/1990 | Oxenrider et al. | 560/87 |
| 5,024,851 A | 6/1991 | Goad et al. | 427/2 |
| 5,027,438 A | 7/1991 | Schwartz et al. | 2/114 |
| 5,035,892 A | 7/1991 | Blank et al. | 424/443 |
| 5,064,613 A | 11/1991 | Higgs et al. | 422/16 |
| 5,073,298 A | 12/1991 | Gentle et al. | 252/358 |
| 5,135,811 A | 8/1992 | White et al. | 428/395 |
| 5,169,625 A | 12/1992 | Blank | |
| 5,244,718 A | 9/1993 | Taylor et al. | 428/229 |
| 5,411,585 A | 5/1995 | Avery et al. | |
| 5,959,014 A | 9/1999 | Liebeskind et al. | 524/389 |

FOREIGN PATENT DOCUMENTS

| | | |
|---|---|---|
| WO | WO9741729 | 11/1997 |
| WO | WO9742200 | 11/1997 |

OTHER PUBLICATIONS

S. F. Hayes and W. C. White, "How Antimicrobial Treatment Can Improve Nonwovens," Reprinted from the *American Dyestuff Reporter* (1984).

(List continued on next page.)

*Primary Examiner*—Robert Dawson
*Assistant Examiner*—Jeffrey B. Robertson
(74) *Attorney, Agent, or Firm*—Saliwanchik, Lloyd & Saliwanchik

(57) ABSTRACT

The composition formed by mixing an organosilane, optionally having a nonhydrolizable organic group, but having one or more hydrolyzable groups, with a polyol containing at least two hydroxy groups, wherein at least any two of the hydroxy groups are separated by no more than two intervening atoms. Water-stabilized organosilane compounds. A water stable composition made from the polyol and organosilane or compound and water. A method of treating a substrate by mixing or contacting the substrate with the product, compound, or composition of this invention for a period of time sufficient for treatment of the substrate. A treated substrate having adhered thereto the product, compound, or composition of this invention. A method of dyeing and treating a substrate. A method of antimicrobially treating a food article. A method of antimicrobially coating a fluid container. A method of antimicrobially coating a latex medical article. A method of making a siloxane in the presence of a stabilizer.

6 Claims, No Drawings

OTHER PUBLICATIONS

R. L. Gettings and B. L. Triplett, "A New, Durable Antimicrobial Finish for Textiles," Reprinted from the 1978 *Book of Paper*, pp 259–261, 1978 American Association of Textile Chemists and Colorists National Technical Conference.

P. A. Walters, E. A. Abbott and A. J. Isquith, "Algicidal Activity of a Surface–Bonded Organosilicon Quaternary Ammonium Chloride," *Applied Microbiology*, 25:253–256 (1973).

J. B. McGee, J. R. Malek and W. C. White, "New Antimicrobial Treatment for Carpet Applications," Reprinted from the Jun. 1983 issue of *American Dyestuff Reporter* by Dow Corning Corp.

A. J. Isquith, E. A. Abbott and P. A. Walters, "Surface–Bonded Antimicrobial Activity of an Organosilicon Quaternary Ammonium Chloride," *Applied Microbiology* 24:859–863 (1972).

Chemical Abstracts 85:125721x (1976).

Chemical Abstracts 83:207489a (1975).

Chemical Abstracts 98:909936b (1983).

Gueyne, C.H.J. et al. (1978) Biologically Active, Water-Soluble Silanes, *Chemical Abstracts*, vol. 88, No. 5, abstract No. 37959n.

* cited by examiner

WATER-STABILIZED ORGANOSILANE COMPOUNDS AND METHODS FOR USING THE SAME

CROSS-REFERENCE TO A RELATED APPLICATION

This is a continuation of application Ser. No. 09/390,008, filed Sep. 3, 1999, now abandoned which is a divisional of application Ser. No. 08/852,474, filed May 7, 1997, now U.S. Pat. No. 5,954,869.

BACKGROUND OF THE INVENTION

1. Field of the Invention:

The invention relates to organosilane compounds, products and methods for their use. In particular, this invention provides water-stable organosilane compounds, products, and compositions for treating various substrates, articles treated with the compounds, products and compositions, and methods of treatment using the compounds, products and compositions.

2. Background:

Organosilanes of the general formula RnSiX4-n where n is an integer of from 0 to 3, but more generally from 0 to 2 (where when n is 3 the organosilanes may only dimerize); R is a organic group, such as, but not limited to, alkyl, aromatic, organofunctional, or a combination thereof, and X is alkoxy, such as methoxy or ethoxy, are prone to self-condensation rendering such organosilanes unstable in water over commercially relevant periods of time. Additionally, X can be a halogen, such as Cl, Br, or I and is similarly liberated as HCl, HBr, or HI. For such organosilanes, the X moiety reacts with various hydroxyl containing molecules in aqueous media to liberate methanol, ethanol, HCl, HBr, HI, $H_2O$, acetic acid, or an unsubstituted or substituted carboxylic acid and to form the hydroxylated, but condensation-prone compound.

For organosilanes $R_nSiX_{4-n}$, where n is an integer from 0 to 2, hydrolysis of the first two X groups with water produces a species bearing —$Si(OH)_2$— units which can self-condense through the hydroxyl moieties to linear and/or cyclic oligomers possessing the partial structure HO—Si—(O—Si)$_{mm}$—O—Si—O—Si—O—Si—OH, where mm is an integer such that an oligomer is formed. For those cases, $RSiX_3$, hydrolysis of the third X group generates a silanetriol ($RSi(OH)_3$) which produces insoluble organosilicon polymers through linear and/or cyclic self-condensation of the Si(OH) units. This water induced self-condensation generally precludes storage of most organosilanes $R_nSiX_{4-n}$, where n ranges from 0 to 2, inclusive, in water. Except for some organosilanes which can be stable in very dilute solutions at specific pH ranges, the use of water solutions of most organosilanes require the use of freshly prepared solutions.

One commercially relevant example of an organosilane suffering from such undesirable self-condensation is the antimicrobial Dow Corning 5700 (Dow Corning Corporation, Midland, Mich.). The literature describes the active ingredient of Dow Corning 5700 as 3-(trimethoxysilyl)propyl-dimethyloctadecyl ammonium chloride. However, in aqueous media, it is believed that the correct active ingredient is more likely 3-(trihydroxysilyl) propyl-dimethyloctadecyl ammonium chloride. Nonetheless, 3-(trimethoxysilyl)propyl-dimethyloctadecyl ammonium chloride is a water activated antimicrobial integrated system which is capable of binding to a wide variety of natural and synthetic substrates, including fibers and fabrics, to produce a durable surface or fabric coating. 3-(Trimethoxysilyl)propyl-dimethyloctadecyl ammonium chloride is prepared by quaternization of dimethyloctadecylamine with 3-chloropropyl trimethoxysilane.

The $C_{18}$ hydrocarbonchain quaternary ammonium portion of the molecule possesses long-acting antimicrobial properties and provides initial association with the surface of the substrate through electrostatic interaction. Preferably, the treated surface becomes permanently coated with a covalently bound octadecylammonium ion, providing a durable, long-acting antimicrobial coating that is able to destroy microbes that come into contact with the surface.

Unfortunately, as noted above, organosilanes in water, such as the activated mixture of 3-(trimethoxysilyl)propyl-dimethyloctadecy ammonium chloride and water, are generally unstable and prone to self-condensation. For instance, the mixture of 3-(trimethoxysilyl)propyl-dimethyloctadecyl ammonium chloride and water begins to lose effectiveness in as little as four to eight hours. Gel formation in this and similar silane formulations in water begins to occur in even shorter times. The limitations of such organosilanes in aqueous media are further described in U.S. Pat. No. 5,411,585, the contents of which are hereby incorporated by this reference. Moreover, such products are notorious for agitation difficulty during the addition of the silane to water. Nevertheless, according to the present invention, clear aqueous gels are considered to be useful compositions.

The use of ammonium silicon compounds as antimicrobial agents in accordance with the prior art is well known and taught in a wide variety of U.S. Pat., Nos. e.g., 3,560,385; 3,794,736; 3,814,739, the contents of which are hereby incorporated by this reference. It is also taught that these compounds possess certain antimicrobial properties which make them valuable and very useful for a variety of surfaces, substrates, instruments and applications (see, e.g., U.S. Pat. Nos. 3,730,701; 3,794,736; 3,860,709; 4,282,366; 4,504,541; 4,615,937; 4,692,374; 4,408,996; and 4,414,268, the contents of which are hereby incorporated by this reference). While these quaternary ammonium silicon compounds have been employed to sterilize or disinfect many surfaces, their employment is still limited because of their toxicity often as a result of the solvent system used to deliver the compound, the necessity for a solvent solution (for instance, Dow Corning antimicrobial agents contain 50% methanol), short term stability (stability of aqueous silane solutions varies from hours to several weeks only) and poor water solubility. For instance, while 3-(trimethoxysilyl)propyl-dimethyloctadecyl ammonium chloride does not suffer from insolubility, it is unstable in water and also, because it is shipped in 50% methanol, it is overly toxic. Many other antimicrobial organosilanes, especially quaternary ammonium silicon compounds, also suffer from problems associated with physical health hazards, e.g., precautions must be taken to avoid contact with both skin and eyes, accidental spills to the surrounding area, flammability, and the added manufacturing steps needed in order to incorporate the such antimicrobial agents into other articles and surfaces, resulting in much higher manufacturing costs.

Therefore, there exists a need for extended shelf-life, water-stable organosilane compounds, products and compositions whereby, upon application, the active portion of the organosilane is operative for the selected application. Moreover, there exists a need for water-stable, organosilane compounds, products and compositions which are essentially non-toxic, non-flammable, uniformly dispersable, and simple and economical to use.

In Provisional Application Serial No. 60/016,985, a method for producing water stable organosilane solutions and compositions is disclosed. According to that invention, stabilization is achieved by reacting the organosilane with a polyol containing at least three hydroxy groups, wherein any two hydroxy groups are separated by at least three intervening atoms. The archetypal example of such a polyol disclosed in that application being pentaerythrytol.

In the instant application, we disclose the finding that compounds having at least two hydroxy groups stabilize aqueous organosilane solutions, even though there are less than three atoms separating at least two of the hydroxyl groups that are present in the polyol. The archetypal example of polyols of the instant invention being glucose, wherein there are several hydroxy groups, several of which are separated by no more than two intervening atoms. According, this invention provides for a much expanded scope of hydroxy containing compounds useful in the stabilization of organosilane compounds.

BRIEF SUMMARY OF THE INVENTION

The present invention fulfills these needs by providing water-stable organosilane compounds, products (i.e., the compounds or compositions formed from performing a specified reaction) and compositions, methods for their use, and articles prepared using the compounds, products, and compositions. The compounds, products, and compositions of the present are toxic, flammable, simple, and economical.

In particular, the present invention provides the product formed from mixing an organosilane of the formula $R_nSiX_{4-n}$ where n is an integer of from 0 to 3, preferably 0 to 2; each R is, independently,a nonhydrolizable organic group; and each X is, independently, a hydrolyzable group; with a polyol containing at least two hydroxy groups wherein any two hydroxy groups of the at least two hydroxy groups present are separated by less than three intervening atoms. Accordingly, alcohols having at least two hydroxyls, carbohydrates, including monosaccharides, disaccharides, oligosaccharides, polysaccharides, modified carbohydrates, including graft and block co-polymers, partially alkylated, partially acylated or partially acetylated carbohydrates, carbohydrate oxidation products (e.g. glucuronic acid, mucic acid), reduced carbohydrates and substituted carbohydrates (e.g. nucleosides, nucleotides, nucleic acids), are all polyols which are useful according to the instant invention.

Accordingly, in one embodiment,this invention provides a water-stable composition, comprising the product or composition of the invention and water.

In a further embodiment, the present invention provides a composition for treating a substrate, comprising a carrier and an effective amount of the product or compound of the invention.

In yet another embodiment, the present invention provides a method of treating a substrate, comprising mixing the substrate with a sufficient amount of the product, compound or composition of the invention for a period of time sufficient for treatment of the substrate.

In a further embodiment, the present invention provides a treated substrate having adhered thereto the product, compound or composition of the invention.

In addition, the present invention provides a method of dyeing and treating a substrate, comprising contacting the substrate with an aqueous composition comprising an aqueous soluble dye suitable for dyeing a substrate and the product formed from mixing an organosilane of the formula $R_nSiX_{4-n}$ where n is an integer of from 0 to 3, preferably 0 to 2; each R is, independently, a nonhydrolizable organic group; and each X is, independently, a hydrolyzable group; with a polyol containing at least two hydroxyls which are separated by less than three intervening atoms, for a period of time sufficient to dye and treat the substrate.

In a further embodiment, the present invention provides a method of antimicrobially treating a food article, comprising contacting or mixing the food article with an effective amount of the product formed from mixing an antimicrobial organosilane of the formula $R_nSiX_{4-n}$ n where n is an integer of from 0 to 3, preferably 0 to 2; each R is, independently, a nonhydrolizableorganic group; and each X is, independently, a hydrolyzable group; with a polyol containing at least two hydroxyls which are separated by less than three intervening atoms, for a period of time sufficient to antimicrobially treat the food article.

In yet another embodiment, the present invention provides a method of antimicrobially coating a fluid container used for containing a human or animal consumable product, comprising contacting the container with an effective amount of the product formed from mixing an antimicrobial organosilane of the formula $R_nSiX_{4-n}$ where n is an integer of from 0 to 3, preferably 0 to 2; each R is, independently, a nonhydrolizable organic group; and each X is, independently, a hydrolyzable group; with a polyol containing at least two hydroxyls which are separated by less than three intervening atoms, for a period of time sufficient to antimicrobially coat the container.

In yet another embodiment, the present invention provides a method of antimicrobially coating a latex medical article for use in a human or animal medical procedure, comprising contacting the article with an effective amount of the product formed from mixing an antimicrobial organosilane of the formula $R_nSiX_{4-n}$ where n is an integer of from 0 to 3, preferably 0 to 2; each R is, independently, a nonhydrolizable organic group; and each X is, independently, a hydrolyzable group; with a polyol containing at least two hydroxyls which are separated by less than three intervening atoms, for a period of time sufficient to antimicrobially coat the article.

A further embodiment of the present invention provides a method of antimicrobially treating a substrate selected the group consisting of a concrete pipe, a tooth brush, a comb, a hair brush, a denture, an orthodontic retainer, a spa or pool filter, an air filter, an HVAC air system, a cabin air system, a marble article, a statue, an exposed work of art, an HDP plastic cover, a silicone or TEFLON® coated fiberglass article, a Dryvitt finish, a stucco finish, blended cotton, a bio-film, a bio-adhesive, a single ply roofing, a roofing shingle, and a fiberglass reinforcement product, comprising contacting the substrate with an effective amount of the product formed from mixing an antimicrobial organosilane of the formula $R_nSiX_{4-n}$ where n is an integer of from 0 to 3, preferably 0 to 2; each R is, independently, a nonhydrolizable organic group; and each X is, independently, a hydrolyzable group; with a polyol containing at least two hydroxyls which are separated by less than three intervening atoms, for a period of time sufficient to antimicrobially treat the substrate.

In addition, the present invention also provides a method of antimicrobially enhancing a product of rubbing alcohol, a flower preservative, or a waterproofing solution, comprising admixing with the product an effective amount of the product formed from mixing an antimicrobial organosilane of the formula $R_nSiX_{4-n}$ where n is an integer of from 0 to 3, preferably 0 to 2; each R is, independently, a nonhydrolizableorganic group; and each X is, independently, a hydrolyzable group; with a polyol containing at least two hydroxyls which are separated by less than three intervening atoms, for a period of time sufficient to antimicrobially enhance the product.

A further embodiment of this invention is a method for making an organosilane of the formula $R_nSiX_{4-n}$ where n is an integer of from 0 to 3, preferably 0 to 2; each R is, independently, a nonhydrolizable orgainc group; and each X is, independently, a hydrolyzable group; from starting materials in an aqueous solution in the presence of a polyol containing at least two hydroxyls which are separated by less than three intervening atoms, in an effective amount of the polyol sufficient to stabilize the organosilane as it is formed from the reactants.

Additional advantages of the invention will be set forth in part in the description which follows, and in part will be obvious from the description, or may be learned by routine practice of the invention as disclosed herein. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DISCLOSURE OF THE INVENTION

The present invention may be understood more readily by reference to the following detailed description of preferred embodiments of the invention.

Before the present compounds, products and compositions and methods are disclosed and described, it is to be understood that the terminology used herein is for the purpose of describing particular embodiments only and is not intended to be limiting. It must be noted that, as used in the specification; and the appended claims, the singular forms "a," "an" and "the" include plural referents unless the context clearly dictates otherwise.

Throughout this application, where publications are referenced, the disclosures of these publications in their entireties are hereby incorporated by reference into this application in order to more fully describe the state of the art to which this invention pertains.

The term "alkyl" as used herein refers to a branched or unbranched saturated hydrocarbon group of 1 to 24 carbon atoms, such as methyl ("Me"), ethyl ("Et"), n-propyl, isopropyl, n-butyl, isobutyl, t-butyl, octyl, decyl, tetradecyl, hexadecyl, eicosyl, tetracosyl and the like. Preferred alkyl groups herein contain from 1 to 12 carbon atoms. The term "lower alkyl" intends an alkyl group of from one to six carbon atoms, preferably from one to four carbon atoms. The term "cycloalkyl" intends a cyclic alkyl group of from three to eight, preferably five or six carbon atoms. "Lower alkyl alcohol" refers to lower alkyl having attached thereto one or more hydroxy moieties, such as, but not limited to, —CH$_2$CH$_2$OH, CH$_2$CH(OH)CH$_3$, CH$_2$OH, CH$_2$CH$_2$CH$_2$OH, CH$_2$CH$_2$CH(OH)CH$_3$, CH$_2$CH$_2$CH(OH)CH$_2$OH, OR CH$_2$CH(OH)CH(OH)CH$_3$.

The term "alkoxy" as used herein intends an alkyl group bound through a single terminal ether linkage; that is, an, "alkoxy" group may be defined as —OR where R is alkyl as defined above. A "lower alkoxy" group intends an alkoxy group containing from one to six, more preferably from one to four, carbon atoms. "Polyether" refers to a compound or moiety possessing multiple ether linkages, such as, but not limited to, polyethylene glycols or polypropylene glycols. "Polyalkylethers " refers to alkyls interconnected by or otherwise possessing multiple ether linkages.

As used herein, "optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyl where there is substitution.

By the term "effective amount" of a compound, product, or composition as provided herein is meant a sufficient amount of the compound, product or composition to provide the desired result. As will be pointed out below, the exact amount required will vary from substrate to substrate, depending on the particular compound, product or composition used, its mode of administration, and the like. Thus, it is not always possible to specify an exact "effective amount." However, an appropriate effective amount may be determined by one of ordinary skill in the art informed by the instant disclosure using only routine experimentation.

The term "aryl" as used herein refers to a compound or moiety whose molecules have a ring or multiple ring structure characteristic of benzene, naphthalene, phenanthrene, anthracene, etc., i.e., either the six-carbon ring of benzene or the condensed six-carbon rings of the other aromatic derivatives, including, but not limited to phenyl, benzyl, naphthyl, benzylidine, xylyl, styrene, styryl, phenethyl, phenylene, benzenetriyl, etc. As used herein, the term "aromatic" refers to the group of unsaturated cyclic hydrocarbons, typified by benzene, having a 6-carbon ring containing three double bonds or multiple attached benzene rings. Moreover, certain five membered cyclic compounds, such as furan (heterocyclic), are analogous to aromatic compounds. Aromatics include the cyclic compounds based upon a benzene functionality, as specified for "aryl" above. Moreover, the term "cyclic" is used to refer to all aliphatic or aromatic hydrocarbons having one or more closed rings, whether unsaturated or saturated. Preferably, cyclic compounds possess rings of from 5 to 7 carbon atoms, preferably 6 carbon atoms. Such rings fall into three classes: alicyclic, aromatic ("arene"), and heterocyclic. Moreover, when used with respect to cyclic compounds or moieties, the term "unsaturated" refers to such compound or moiety possessing at least one double or triple bond or otherwise constituting an aromatic compound or moiety. Moreover, the term "saturated" refers to compounds or moieties possessing no double or triple bonds, i.e., where all available valence bonds of an atom, especially carbon, are attached to other atoms.

The term "heteroaryl" refers to an aryl where one or more of the carbon atoms of a ring have been substituted with a heteroatom, including, but not limited to, O, N, or S. Similarly, the term "heterocyclic" refers to a cyclic compound or moiety where one or more of the carbon atoms of the ring has been substituted with a heteroatom, including, but not limited to O, N, or S.

As used herein, especially in reference to alkyl and alkoxy, the term "lower" refers to a moiety having from 1 to 6 carbon atoms, preferably 1 to 4 carbon atoms.

As used herein, the term "suitable" is used to refer a moiety which is compatible with the compounds, products, or compositions as provided herein for the stated purpose. Suitability for the stated purpose may be determined by one of ordinary skill in the ar using only routine experimentation.

As used herein, "substituted" is used to refer, generally, to a carbon or suitable heteroatom having a hydrogen or other atom removed and replaced with a further moiety. In one embodiment, halogen, hydroxy, and nitrogen based substitutions of hydrocarbon hydrogens are contemplated as within the scope of the present invention for the claimed structures. Moreover, it is intended that "substituted" refer to substitutions which do not change the basic and novel utility of the underlying compounds, products or compositions of the present invention. "Unsubstituted" refers to a structure wherein the reference atom does not have any further moieties attached thereto or substituted therefor.

As used herein, "branched" is used to refer, generally, to a moiety having a carbon chain backbone, e.g., alkyl or alkoxy, wherein the backbone may contain one or more subordinate carbon chain branches. For example, isobutyl, t-butyl, isopropyl, $CH_2CH_2C(CH_3)(H)CH_2CH_3$, $CH_2C(CH_2CH_3)(H)CH_2CH_3$, $CH_2CH_2C(CH_3)CH_3$, and $CH_2CH_2C(CH_3)_3$ would all be considered branched moieties. Moreover, it is intended that "branched" variations of the moieties herein described refer to variations which do not change the basic and novel utility of the underlying compounds, products or compositions of the present invention. "Unbranched" refers to a structure wherein the carbon chain does not have any branches thereon, i.e., where the carbon chain extends in a direct line.

As used herein, the term "acyl" refers to organic acid derived moieties of the formula RCOX where R is an organic molecule and X, instead of being hydroxy, is replaced with another substituent, preferably, a suitable anion.

As used herein, the term "perfluoro" or "perfluoro-analog" refers to a hydrocarbon where the hydrogen atoms attached to carbons have been replaced with F atoms. Preferably, but not necessarily, in perfluoro-analogs, most if not all of the H atoms are replaced with F atoms. A "fluoro-" analog is contemplated to indicate a hydrocarbon where at least one hydrogen atom attached to a carbon is replaced with an F atom.

As used herein, "substrate" refers to any article, product, or other surface that can be treated with the inventive compounds, preferably as enumerated herein below under the heading Uses, as described in the Examples hereto, and as specified in the relevant claims appended hereto. Suitable substrates are generally characterized in preferably having a negatively charged surface of oxygen atoms, or any surface capable of electrostatically, ionically or covalently adhering or binding to the compounds, products, or compositions of the present invention. Preferably the adhering or binding occurs at the silicon atoms of the organosilane portion of the compounds, products, or compositions of the present invention, but such binding is not a requirement. Therefore, as used herein, the term "adhere" is meant to refer to ionic, covalent, electrostatic, or other chemical attachment of a compound, product or composition to a substrate.

As used herein, the term "antimicrobially enhancing" refers to the use of the compounds, products, or compositions of the present invention, preferably those wherein the organosilane has antimicrobial activity, along with other ingredients, surfactants, fillers, wetting agents, pigments, dyes, antimigrants, etc., to create a composition or solution capable of fulfilling its original purpose, based upon the other ingredients, and also of providing antimicrobial protection during the particular application. The term "enhance" refers to the addition of antimicrobial activity to such compositions or solutions where no such activity previously existed, or to the increase of antimicrobial activity wherein the starting compositions or solutions inherently possessed antimicrobial activity.

As used herein, "hydrolyzable" refers to whether the moiety is capable of or prone to hydrolysis (i.e., splitting of the molecule or moiety into two or more new molecules or moieties) in aqueous or other suitable media. Conversely, "nonhydrolizable" refers to moieties that are not prone to or capable of hydrolysis in aqueous or other suitable media.

As used herein, "cationic" is used to refer to any compound, ion or moiety possessing a positive charge. Moreover, "anionic" is used to refer to any compound, ion or moiety possessing a negative charge. Furthermore, "monovalent" and "divalent" are used to refer to moieties having valances of one and two, respectively. Moreover, as used herein, the term "salt" is meant to apply in its generally defined sense as "compound formed by replacing all or part of the hydrogen ions of an acid with one or more cations of a base." See, e.g., American Heritage Dictionary, Definition of "Salt" (1981). Therefore, suitable salts forte present invention may be formed by replacing a hydrogen ion of a moiety with a cation, such as $K^+$, $Na^+$, $Ca^{2+}$, $Mg^{2+}$, etc. In addition, other suitable methods of generating salts are specified throughout this specification and are within the scope of the present definition. It is believed that, for the purposes of the present invention, the specific identity of the cation used for forming the salt is of lesser importance than the chemical structure of the anion of which the salt is formed.

As used herein, "food article" refers to perishable or nonperishable foods such as meats, fruits and vegetables, and also refers to other foods such as grains and dairy products. In preferable embodiments, the food articles referred to herein are those which are perishable or prone to spoilage upon exposure to microbes or other pathogens. In addition, a "consumable product" is meant to refer to food articles, fluids for drinking, medicines for ingestion or any other product introduced internally via any means into a human or animal.

As used herein, the term "antimicrobial" is used in its general sense to refer to the property of the described compound, product, composition or article to prevent or reduce the growth, spread, formation or other livelihood of organisms such as bacteria, viruses, protozoa, molds, or other organisms likely to cause spoilage or infection.

As used herein, the term "medical article" is used to refer to any suitable substrate which is or may come into contact with medical patients (human or animal), medical care givers, bodily fluids, or any other source of contamination or infection generally associated with hospitals, clinics, physician's offices, etc.

As used herein, the term "stabilizer" is used to refer to the class of polyols containing at least two hydroxyls which are separated by less than three intervening atoms. Such compounds have been found to stabilize the organosilanes of the invention by preventing self-condensation or other inactivation of the resulting compounds and products.

As used herein, the terms "polyol" and "stabilizer" are used interchangeably to describe a molecule having at least two hydroxyls separated by no more than two atoms.

Finally, the terms "halogen" are used to refer to Fluorine "F", Chlorine "Cl", Bromine "Br". Iodine "I", and Astatine "At". Preferably, halogen or halide refers to F, Cl, or Br. The term "halide" is meant to include these halogens.

With these definitions in mind, the present invention provides the product formed from mixing an organosilane of the formula $R_nSiX_{4-n}$ where n is an integer of from 0 to 3, preferably 0 to 2; each R is, independently, a nonhydrolizableorganic group; and each X is, independently, a hydrolyzable group; with a polyol containing at least two hydroxyls which are separated by less than three intervening atoms (i.e. regardless of the total number of hydroxy groups in the compound, there are at least two which are separated by less than three intervening atoms).

More preferably, in the above product, n is an integer from 0 to 2, preferably 1; each R is, independently, alkyl, preferably of from 1 to 22 carbon atoms branched or unbranched, substituted or unsubstituted, more preferably of from 1 to 6 carbon atoms or from 10 to 20 carbon atoms, most preferably of from 1 to 4 carbon atoms or of from 14 to 18 carbon atoms; alkyl alcohol of similar carbon lengths, branching and substitution, or aromatic, such as benzyl, phenyl, etc.; each X is, independently, hydroxy, alkoxy, halogen (such as, but not limited to, Cl, Br, l, or F), acetyl, acetoxy, acyl, a hydroxylated solid or liquid polymeric moiety, polyether or polyalkylether; and the polyol is an alcohol having at least two hydroxyls, a carbohydrate, including a monosaccharide, a disaccharide, an oligosaccharide, a polysaccharide, a modified carbohydrate, including a graft or block co-polymers, a partially alkylated, acylated or acetylated carbohydrate, a carbohydrate oxidation product (e.g. glucuronic acid, mucic acid), reduced carbohydrates, substituted carbohydrate or substituted carbohydrate polymers (e.g. nucleosides, nucleotides, nucleic acids). In one embodiment, the polyol is a simple monosaccharide, such as glucose, fucose, fructose. In a further embodiment, the polyol is an oligomeric sugar (e.g. a dimer, such as sucrose, a trimer, a tetramer, etc). In another embodiment, the polyol is mannitol, ascorbic acid, glyoxal or a nucleoside. Where ascorbic acid or like compound is used as the polyol, it is frequently desirable to include an anti-oxidant in the composition, to prevent oxidation of the ascorbic acid. In another embodiment, the polyol is an oxidized sugar, such as glucuronic acid. In another embodiment, the polyol is a polymeric carbohydrate, such as cellulose, partially hydrolyzed cellulose, partially hydrolyzed cellulose acetate, starch, soluble starch, a starch acrylic acid graft copolymer. As a source of certain of these polyols, cost-effective carbohydrate and even complex carbohydrate compositions include corn syrup, honey or like compositions. In order to control bacterial growth, these compositions may optionally include a preservative, such as benzoic acid, which is acceptable for human applications, and which provides an antibacterial function. This is particularly important where the organosilane to be stabilized does not itself have antimicrobial activity, and is much less significant where the organosilane itself is antibacterial.

In a further embodiment of the present invention, the invention provides the product described above, wherein the organosilane is of the formula II, III, IV, or V:

(II)

(III)

(IV)

(V)

wherein each $R_1$ is, independently, halogen or $R_6O$, where $R_6$ is H, alkyl of from 1 to about 22 carbon atoms, acetyl, acetoxy, acyl, propylene glycol, ethylene glycol, polyethylene glycol, polypropylene glycol; block and copolymers of ethylene and propylene glycol, the alkyl monoether of from 1 to 22 carbons of propylene: glycol, ethylene glycol, polyethylene glycol, polypropylene glycol; block and copolymers of ethylene and propylene glycol or the monoester of a carbonic acid of from 1 to 22 carbons and propylene glycol, ethylene glycol, polyethylene glycol, polypropylene glycol; block and copolymers of ethylene and propylene glycol; octyphenol; nonylphenol; and sorbitan ethers;

$R_{35}$ is H, halogen (such as Cl, Br, F, or I), $NH_2(CH_2)_2NH$, $NH_2$, $C_3H_5O_2$, $C_4H_5O_2$, $NaO(CH_3O)P(O)$, or $ClCH_2C_6H_4$; $R_{36}$ and $R_{37}$ are, independently, halogen, H, alkyl of from 1 to about 8 carbon atoms, preferably of from 1 to 4 carbon atoms, more preferably of from 1 to 2 carbon atoms, isobutyl, phenyl, or n-octyl; $R_2$ is benzyl, vinyl or alkyl of from 1 to about 3 carbon atoms; $R_3$ and $R_4$ are, independently, lower alkyl alcohol of from 1 to 4 carbon atoms, lower alkoxy of from 1 to 4 carbon atoms, alkyl of from 1 to about 22 carbon atoms, preferably 1 to about 10 carbon atoms, more preferably alkyl of from 1 to 4 carbon atoms, or more preferably of from 1 to 2 carbon atoms; or $R_3$ and $R_4$ can, together, form a morpholine or cyclic or heterocyclic, unsaturated or saturated, five to seven-membered ring of the formula VI:

(VI)

where k is an integer from 0 to 2, preferably 0 to 1, most preferably 1, $R_7$, where the ring is saturated, is $CH_2$, O, S, NH, $NH_2^+$, $NCH_2CH_2NH_2$, $NCH_2CH_2NH_3^+$, $NCH_2CH_2N(R_8)(R_9)$, $NCH_2CH_2N^+(R_8)(R_9)(R_{10})$, N(alkyl), N(aryl), N(benzyl), where each $R_8$, $R_9$, and $R_{10}$ is, independently, benzyl, polyether, lower alkyl alcohol of from 1 to 4 carbon atoms, lower alkoxy of from 1 to 4 carbon atoms, or alkyl of from 1 to about 22 carbon atoms, preferably 1 to about 10 carbon atoms, and the "alkyl" specified. above is of from 1 to 22 carbon atoms, more preferably of from 1 to 10 carbon atoms, most preferably of from 1 to 3 carbon atoms, the "aryl" is more preferably phenyl or benzyl, and $R_7$, where the ring is unsaturated is, CH, N, $N^+H$, $N^+(alkyl)$, $N^+(aryl)$, $N^+(benzyl)$, $N-CH_2-N$, $N^+H-CH_2-N$, $N^+(alkyl)-CH_2-N$, $N^+(aryl)-CH_2-N$, or $N^+(benzyl)-CH_2-N$ where the alkyl, aryl, or benzyl is as described above; wherein the ring is unsubstituted or substituted with alkyl of from 21 to 22 carbon atoms, more preferably of from 1 to 10 carbon atoms, most preferably of from 1 to 3 carbon atoms, ester, aldehyde, carboxylate (preferably acetoxy, acetyl, acyl or perfluorocarboxylate), amide, thionamide, nitro, amine, or halide, most preferably Cl, Br, or I; $R_5$ is lower alkyl alcohol, preferably of from 1 to 6 carbon atoms, more preferably of from 1 to 4 carbon atoms, $CH_2C_6H_5$, polyether, such as a polyethyleneglycol or a polypropylene glycol, alkyl of from 1 to 22 carbon atoms, more preferably of from 1 to 10 carbon atoms, most preferably of from 1 to 6 carbon atoms, alkoxy, of from 1 to 22 carbon atoms, more preferably of from 1 to 10 carbon atoms, most preferably of from 11 to 6 carbon atoms, perfluoroalkyl, of from 1 to 22 carbon atoms, more preferably of from 1 to 10 carbon atoms, most preferably of from 1 to 6 carbon atoms, perfluoroalkylsulfonate, of from 1 to 22 carbon atoms, more preferably of from 1 to 10 carbon atoms, most preferably of from 1 to 6 carbon atoms, or perfluoroalkylcarboxylate, or is a five to seven-membered ring of formula VI as described above; and Y⁻ is a suitable anionic moiety to form the salt of the compound of formula II, III, IV or V.

This invention provides a water stable composition, comprising water and the organosilane, mixed with the polyol.

In addition, the present invention also provides a composition for treating a substrate, comprising a carrier and an effective amount of an organosilane and a polyol as described herein. In an alternate embodiment, the present invention provides a composition for treating a substrate, comprising a carrier and an effective amount of the compound as described above. In further embodiments, the carrier is other than water.

In a further embodiment, the organosilane is
3-(trimethoxysilyl)propyldimethyloctadecyl ammonium chloride,
3-(trimethoxysilyl)propylmethyldi(decyl) ammonium chloride,
3-chloropropyltrimethoxysilane, octadecyltrimethoxysilane, or perfluorooctyltriethoxysilane
and the polyol is an alcohol having at least two hydroxyls, carbohydrates, including monosaccharides, disaccharides, oligosaccharides, polysaccharides, modified carbohydrates, including graft and copolymers, partially alkylated, acylated or acetylated carbohydrates, carbohydrate oxidation products (e.g. glucuronic acid, mucic acid), reduced carbohydrates and substituted carbohydrates (e.g. nucleosides, nucleotides, nucleic acids).

In yet another embodiment, the organosilane is
$(CH_3O)_3Si(CH_2)_3N^+(CH_3)_2C_{18}H_{37}Cl^-$, $(CH_3O)_3Si(CH_2)_3N^+(CH_3)_2C_{18}H_{37}Br^-$,
$(CH_3O)_3Si(CH_2)_3N^+(C_{10}H_{21})_2CH_3Cl^-$, $(CH_3O)_3Si(CH_2)_3N^{30}(C_{10}H_{21})_2CH_3BR^-$,
$(CH_3O)_3Si(CH_2)_3N^+(CH_3)_3Cl^-$, $(CH_3O)_3Si(CH_2)_3N^{30}(CH_3)_2C_8H_{17}Cl^-$,
$(CH_3O)_3Si(CH_2)_3N^+(CH_3)_2C_{10}H_{21}Cl^-$, $(CH_3O)_3Si(CH_2)_3N^+(CH_3)_2C_{12}H_{25}Cl^-$,
$(CH_3O)_3Si(CH_2)_3N^+(CH_3)_2C_{14}H_{29}Cl^-$, $(CH_3O)_3Si(CH_2)_3N^+(CH_3)_2C_{16}H_{33}Cl^-$,
$(CH_3O)_3Si(CH_2)_3N^+(CH_3)_2C_{20}H_{41}Cl^-(CH_3O)_3Si(CH_2)_3N^+(CH_4h_9)_3Cl^-$,
$(CH_3O)_3Si(CH_2)_3N^+(C_2H_5)_3Cl^-(CH_3CH_2O)_3Si(CH_2)_3N^+(CH_3)_2C_{18}H_{37}Cl^-$, carbohydrates, carbohydrate oxidation products (e.g. glucuronic acid, music acid), reduced carbohydrates and substituted carbohydrates (e.g. nucleosides, nucleotides, nucleic acids).
$(CH_3O)_3Si(CH_2)_3NHC(O)(CF_2)_6CF_3$, $(CH_3O)_3Si(CH_2)_3NHC(O)(CF_2)_8CF_3$,
$(CH_3O)_3Si(CH_2)_3NHC(O)(CF_2)_{10}CF_3$, $(CH_3O)_3Si(CH_2)_3NHC(O)(CF_2)_{12}CF_3$,
$(CH_3O)_3Si(CH_2)_3NHC(O)(CF_2)_{14}CF_3(CH_3O)_3Si(CH_2)_3NHC(O)(CF_2)_{16}CF_3$,
$(CH_3O)_3Si(CH_2)_3NHSO_2(CF_2)_7CF_3$,
$(CH_3O)_3Si(CH_2)_3N^+(CH_3)_2(CH_2)_3NHC(O)(CH_2)_6CH_3$,
$(CH_3O)_3Si(CH_2)_3N^+(CH_3)_2(CH_2)_3NHC(O)(CH_2)_8CH_3$,
$(CH_3O)_3Si(CH_2)_3N^+(CH_3)_2(CH_2)_3NHC(O)(CH_2)_{10}CH_3$,
$(CH_3O)_3Si(CH_2)_3N^+(CH_3)_2(CH_2)_3NHC(O)(CH_2)_{12}CH_3$,
$(CH_3O)_3Si(CH_2)_3N^+(CH_3)_2(CH_2)_3NHC(O)(CH_2)_{14}CH_3$,
$(CH_3O)_3Si(CH_2)_3N^+(CH_3)_2(CH_2)_3NHC(O)(CH_2)_{16}CH_3$,
$(CH_3O)_3Si(CH_2)_3N^+(CH_3)_2(CH_2)_3NHC(O)(CF_2)_6CF_3$,
$(CH_3O)_3Si(CH_2)_3N^+(CH_3)_2(CH_2)_3NHC(O)(CF_2)_8CF_3$,
$(CH_3O)_3Si(CH_2)_3N^+(CH_3)_2(CH_2)_3NHC(O)(CF_2)_{10}CF_3$,
$(CH_3O)_3Si(CH_2)_3N^+(CH_3)_2(CH_2)_3NHC(O)(CF_2)_{12}CF_3$,
$(CH_3O)_3Si(CH_2)_3N^+(CH_3)_2(CH_2)_3NHC(O)(CF_2)_{14}CF_3$,
$(CH_3O)_3Si(CH_2)_3N^+(CH_3)_2(CH_2)_3NHC(O)(CF_2)_{16}CF_3$,
$(CH_3O)_3Si(CH_2)_3N^+(CH_3)_2(CH_2)_3NHSO_2(CF_2)_7CF_3$,
$(CH_3O)_3Si(CH_2)_3N^+(CH_3)_2(CH_2)_3NHSO_2(CF_2)_9CF_3$,
$(CH_3O)_3Si(CH_2)_3N^+(CH_3)_2(CH_2)_3NHSO_2(CF_2)_{11}CF_3$,
$(CH_3O)_3Si(CH_2)_3N^+(CH_3)_2(CH_2)_3NHSO_2(CF_2)_{13}CF_3$,
$(CH_3O)_3Si(CH_2)_3N^+(CH_3)_2(CH_2)_3NHSO_2(CF_2)_{15}CF_3$, or
$(CH_3O)_3Si(CH_2)_3N^+(CH_3)_2(CH_2)_3NHSO_2(CF_2)_{16}CF_3$, and block co-polymers, partially alkylated, acylated or acetylated carbohydrates, carbohydrate oxidation products (e.g. glucuronic acid, mucic acid), reduced carbohydrates and substituted carbohydrates.(e.g. nucleosides, nucleotides, nucleic acids).

In addition, the present invention also provides a method of treating a substrate, comprising contacting the substrate with a sufficient amount of the composition as described above for a period of time sufficient for treatment of the substrate. Moreover, in an alternate embodiment, the present invention provides a method of treating a substrate, comprising contacting the substrate with a sufficient amount of the compound as described above for a period of time sufficient for treatment of the substrate.

In addition, the present invention provides a treated substrate having adhered thereto the product produced by contacting the organosilane and the polyol as described above. Alternatively, the present invention provides a treated substrate having adhered thereto a compound produced by contacting the organosilane and the polyol as described above.

In yet another embodiment, the present invention provides a method of dyeing and treating a substrate, comprising contacting the substrate with an aqueous (i.e., substantially water soluble) composition comprising an aqueous soluble dye suitable for dyeing a substrate and the product formed from mixing an organosilane of the formula $R_nSiX_{4-n}$ where n is an integer of from 0 to 3, preferably 0 to 2; each R is, independently, a nonhydrolizable organic group; and each X is, independently, a hydrolyzable group; with a polyol comprising at least two hydroxy groups, wherein at least two such groups are separated by less than three intervening atoms, for a period of time sufficient to dye and treat the substrate.

In a further preferred embodiment, the present invention provides a method of antimicrobially treating a food article, comprising contacting the food article with an effective amount of the product formed from mixing an antimicrobial organosilane of the formula $R_nSiX_{4-n}$ where n is an integer of from 0 to 3, preferably 0 to 2; each R is, independently, a nonhydrolizable organic group; and each X is, independently, a hydrolyzable group; with a polyol comprising at least two hydroxy groups, wherein at least two such groups are separated by less than three intervening atoms, for a period of time sufficient to antimicrobially treat the food article.

In yet another embodiment, the present invention provides a method of antimicrobially coating a fluid container used for containing a human or animal consumable product, comprising contacting the container with an effective amount of the product formed from mixing an antimicrobial organosilane of the formula $R_nSiX_{4-n}$ where n is an integer of from 0 to 3, preferably 0 to 2; each R is, independently, a nonhydrolizable organic group; and each X is, independently, a hydrolyzable group; with a polyol comprising at least two hydroxy groups, wherein at least two such groups are separated by less than three intervening atoms, for a period of time sufficient to antimicrobially coat the container.

Moreover, in yet another embodiment, the present invention provides a method of antimicrobially coating a latex medical article for use in a human or animal medical procedure, comprising contactiring the article with an effective amount of the product formed from mixing an antimicrobial organosilane of the formula $R_nSiX_{4-n}$ where n is an integer of from 0 to 3, preferably 0 to 2; each R is, independently, a nonhydrolizable organic group; and each X is, independently, a hydrolyzable group; with a polyol comprising at least two hydroxy groups, wherein at least two such groups are separated by less than three intervening atoms, for a period of time sufficient to antimicrobially coat the article. In a further embodiment of this method, the article is a surgical glove.

In yet another embodiment, the present invention provides a method of antimicrobially treating a substrate selected from the group consisting of a concrete pipe, a tooth brush, a comb, a hair brush, a denture, an orthodontic retainer, a spa or pool filter, an air filter, an HVAC air system, a cabin air system, a marble article, a statue, an exposed work of art, an HDP plastic cover, a silicone or TEFLON® coated fiberglass article, a Dryvitt finish, a stucco finish, blended cotton, a bio-film, a bio-adhesive, a single ply roofing, a roofing shingle, and a fiberglass reinforcement product, comprising contacting the substrate with an effective amount of the product formed from mixing an antimicrobial organosilane of the formula $R_nSiX_{4-n}$ where n is an integer of from 0 to 3, preferably 0 to 2; each R is, independently, a nonhydrolizable organic group; and each X is, independently, a hydrolyzable group; with a polyol comprising at least two hydroxy groups, wherein at least two such groups are separated by less than three intervening atoms, for a period of time sufficient to antimicrobially treat the substrate.

Moreover, in yet another embodiment, the present invention provides a method of antimicrobially enhancing a product of rubbing alcohol, a flower preservative, or a waterproofing solution, comprising admixing with the product an effective amount of the product formed from mixing an antimicrobial organosilane of the formula $R_nSiX_{4-n}$ where n is an integer of from 0 to 3, preferably 0 to 2; each R is, independently, a nonhydrolizable organic group; and each X is, independently a hydrolyzable group; with a polyol comprising at least two hydroxy groups, wherein at least two such groups are separated by less than three intervening atoms, for a period of time sufficient to antimicrobially enhance the product.

The present invention provides water-stabilized and/or solubilized organosilane compounds, products and compositions, methods of their use, and articles prepared using the compounds, products and compositions. In particular, the present invention is useful in stabilizing a broad variety of organosilanes of the general formula $R_nSiX_{4-n}$ where n is an integer of from 0 to 3, preferably 0 to 2; R is a nonhydrolizable organic group, such as but not limited to, alkyl, aromatic, organofunctional, or a combination thereof, and X is halogen, such as but not limited to, Cl, Br, or I, or X is hydroxy, alkoxy such as methoxy or ethoxy, acetoxy, or unsubstituted or substituted acyl. For such organosilanes, X is prone to react with various hydroxyl containing molecules.

In a further embodiment, the present invention employs from about 0.001% to about 20% by weight of an organosilane containing hydrolyzable groups and from about 0.01 to about 20.0 weight equivalents, preferably from about 0.1 to about 5 weight equivalents of a polyol stabilizer of the invention. This preparation is preferable for water soluble stabilizers, such as glucose, sucrose, glucuronic acid, nucleosides, nucleotides, polynucleotides. Alternatively, where the stabilizers are not sufficiently water-soluble, additional stability is achieved by mixing the organosilane with the stabilizer in a non-aqueous solvent. In such an alternative preparation, the remaining solvent (e.g., methanol) is liberated via distillation, freeze-drying, evaporation or other methods known in the art for removal or volatile organic solvents. For polyols within this invention that arc themselves not very soluble in water, an organosilane stabilizing effect may still be achieved by admixing the organosilane with, for example, a carbohydrate in water, followed by filtration. The filtrate may thus be stabilized while still exhibiting a desirable property, such as antimicrobial activity. Where the organosilane is not an antimicrobial agent, spectral evidence of the compound's presence is useful to demonstrate the compound's presence. These methods provide stable, clear solutions of the organosilane which are capable of coating surfaces with the organosilane upon treatment of the surface with the solution.

The solutions are stable for extended periods, from several days to several months. It will also be recognized that while aqueous siloxane stock solutions of up to 20% siloxane may be stabilized by polyols disclosed herein, working siloxane concentrations tend to be in the 0.001–5% siloxane range where the stabilization effects of the herein disclosed stabilizers are less challenged by the higher siloxane concentrations required in stock solutions.

The solutions of the present invention are, in certain preferred embodiments, useful for the application of various organosilane coupling agents to surfaces in industrial and household uses without the use of toxic and/or flammable organic solvents. One of ordinary skill in the art would recognize that the above preparation steps are merely guidelines and such a person would, without undue experimentation, be able to prepare the composition by varying the parameters for contacting or mixing the organosilane and the polyol and order of introduction of reagents and starting materials without deviating from the basic and novel characteristics of the present invention.

Silanes

The present invention is useful for stabilizing organosilanes of the general formula where n is an integer of from 0 to 3, preferably 0 to 2; R is a nonhydrolizable organic group (alkyl, aromatic, organofunctional or a combination thereof); and X is hydroxy, alkoxy, preferably methoxy or ethoxy, halogen, preferably Cl, Br, or I, acetoxy, acyl or substituted acyl, or a hydrolyzable polymer or other moiety prone to hydrolysis and/or environmental harmfulness.

The organosilanes used in the practice of the present invention need not be, and often are not, water soluble. By varying the stabilizer and preparation method, the organosilanes selected for use in the present invention are solubilized in water by the stabilizer.

Numerous art-known organosilanes are suitable for the present stabilization procedures to produce water-stabilized compounds, products and compositions. U.S. Pat. Nos. 4,511,885; 5,064,613; 5,145,592, and the publication entitled "A Guide to DC Silane Coupling Agent+ (Dow Coming, 1990) disclose many suitable organosilanes. The contents of these references are hereby incorporated in their entirety herein by this reference for the teachings of suitable organosilanes. These organosilanes are suitable for the formation of the water-stabilized organosilane compounds, products and compositions of the present invention. In addition, the disclosure of U.S. Pat. No. 4,390,712 is hereby incorporated by reference for its teaching of siloxane synthesis in an aqueous medium. Per the instant disclosure, those skilled in the art will appreciate that the aqueous siloxane synthesis methods of the U.S. Pat. No. 4,390,712 are modified to advantage by performing the siloxane synthesis in the presence of the polyol stabilizer as defined herein, thereby forming a stabilized siloxane-water composition while still taking advantage of the accelerated kinetics of siloxane formation in aqueous media noted in the U.S. Pat. No. 4,390,712. Accordingly, a further embodiment of this invention is a method for making an organosilane of the formula $R_nSiX_{4-n}$ where n is an integer of from 0 to 3, preferably 0 to 2; each R is, independently, a nonhydrolizable organic group; and each X is, independently, a hydrolyzable group; from starting materials in an aqueous solution in the presence of a polyol containing at least two hydroxyls which are separated by less than three intervening atoms in an effective amount of the polyol sufficient to stabilize the organosilane as it is formed from the reactants.

Preferred silanes for use in the compounds, products and compositions and methods of the present invention include silanes of the following formula:

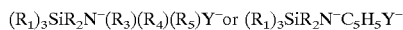

$(R_1)_3SiR_2N^-(R_3)(R_4)(R_5)Y^-$ or $(R_1)_3SiR_2N^-C_5H_5Y^-$ wherein each $R_1$ is, independently, halogen [Cl, Br, I, F] or $R_6O$, where $R_6$ is H, alkyl of from 1 to about 6 carbon atoms, unsubstituted or substituted, preferably from 1 to about 2 carbon atoms and more preferably 1 carbon atom, or acetyl- or other acyl, including substituted acyl, or $R_6O$ can be derived from any hydroxylated polymer, hydroxylated liquid, or hydroxylated solid regardless of water solubility, or $R_6O$ can be derived from any polyether such as, but not limited to, polyethyleneglycols or polypropyleneglycols, such as poly(propyleneglycol)triol (glycerol propoxylate); $R_2$ is unsubstituted or substituted benzyl- or of from 1 to 22 carbon atoms; $R_3$ and $R_4$ are, independently, lower alkoxy of from 1 to 4 carbon atoms, preferably of 2 carbon atoms, such as $CH_2CH_2OH$, $CH_2CH(OH)CH_3$, alkyl of from 1 to about 22 carbon atoms, preferably from 1 to about 10 carbon atoms and most preferably from 1 to 2 carbon atoms or $R_3$ and $R_4$ can, together, form a morpholine or other cyclic or heterocyclic, unsaturated or saturated, five to seven-membered ring of the formula:

—$R_3$—$(R_7)_k$—$R_4$— where k is an integer from 0 to 2 and $R_7$, where the ring is saturated, is $CH_2$, O, S, NH, $NH_2^-$, $NCH_2CH_2NH_2$, $NCH^?CH_2NH_3^{-,}$  $^{NCH}{}_2CH_2N(R_8)(R_9)$, $NCH_2CH_2N^+(R_8)(R_9)(R_{10})$, N(alkyl), N(aryl), N(benzyl), and $R_7$, where the ring is unsaturated is, N, $N^+H$, $N^+$(alkyl), $N^+$(aryl), $N^+$(benzyl), N—$CH_2$—N, $N^{-H-CH}{}_2$—N, $N^+$(alkyl)-$CH_2$—N, $N^+$(aryl)-$CH_2$—N, or $N^-$(benzyl)-$CH_2$, —N where $R_8$, $R_9$, and $R_{10}$, are, independently, benzyl, polyether, lower alkyl alcohol of from 1 to 4 carbon atoms, lower alkoxy of from 1 to 4 carbon atoms, or alkyl of from 1 to about 22 carbon atoms, preferably 1 to about 10 carbon atoms; $R_5$ is $CH_2C_6H_5$, $CH_2CH_2OH$, $CH_2CH(OH)CH_3$, a polyether such as polyethyleneglycol: —$(CH_2CH_2O)_aH$, polypropyleneglycol: —$(CH_2CH(CH_3)O)_aH$, or alkylated polyoxyethylene: —$(CH_2CH_2O)_aB$ where B is alkyl of from 1 to 22 carbon atoms, unsubstituted or substituted, and where each a is, independently, an integer of from 1 to 12, more preferably of from about 1 to about 5, or $R_5$ is alkyl or perfluoroalkyl of from 1 to about 22 carbon atoms, preferably from about 12 to about 20 carbon atoms and even more preferably from 14 to about 18 carbon atoms; and Y is halogen (such as Cl, Br, I), acetate, sulfate, tosylate or carboxylate, such as acetate, polycarboxylate salts, functionalized carboxylate, such as trifluoroacetate and perfluoroalkylcarboxylates, or other alkyl and arylsulfonate salts, including trifluoromethylsulfonate and perfluoroalkylsulfonatesalts, phosphate and phosphonate salts, borate and boronate salts or any other suitable anionic moiety.

Preferred organosilanes include, but are not limited to:
3-(trimethoxysilyl)propyldimethyloctadecyl ammonium chloride,
3-(trimethoxysilyl)propylmethyldi(decyl) ammonium chloride,
3-chloropropyltrimethoxylsilane,
octadecyltrimethoxysilane,
perfluorooctyltriethoxysilane,
$(CH_3O)_3Si(CH_2)_3N^+(CH_3)_2C_{18}H_{37}Cl^-$,
$(CH_3O)_3Si(CH_2)_3N^+(CH_3)_2C_{18}H_{37}Br^-$,
$(CH_3O)_3Si(CH_2)_3N^+(C_{10}H_{21})_2CH_3Cl^-$,
$(CH_3O)_3Si(CH_2)_3N^+(C_{10}H_{21})_2CH_3Br^-$,
$(CH_3O)_3Si(CH_2)_3N^+(CH_3)_3Cl^-$,
$(CH_3O)_3Si(CH_2)_3N^+(CH_3)_2C_8H_{17}Cl^-$,
$(CH_3O)_3Si(CH_2)_3N^+(CH_3)_2C_{10}H_{21}Cl^-$,
$(CH_3O)_3Si(CH_2)_3N^+(CH_3)_2C_{12}H_{25}Cl^-$,
$(CH_3O)_3Si(CH_2)_3N^+(CH_3)_2C_{14}H_{29}Cl^-$,
$(CH_3O)_3Si(CH_2)_3N^+(CH_3)_2C_{16}H_{33}Cl^-$,
$(CH_3O)_3Si(CH_2)_3N^+(CH_3)_2C_{20}H_{41}Cl^-$,
$(CH_3O)_3Si(CH_2)_3N^+(C_4H_9)_3Cl^-$,
$(CH_3O)_3Si(CH_2)_3N^+(C_2H_5)_3Cl^-$,
$(CH_3CH_2O)_3Si(CH_2)_3N^+(CH_3)_2C_{18}H_{37}Cl^-$,
$(CH_3O)_3Si(CH_2)_3NHC(O)(CF_2)_6CF_3$,
$(CH_3O)_3Si(CH_2)_3NHC(O)(CF_2)_8CF_3$,
$(CH_3O)_3Si(CH_2)_3NHC(O)(CF_2)_{10}CF_3$,
$(CH_3O)_3Si(CH_2)_3NHC(O)(CF_2)_{12}CF_3$,
$(CH_3O)_3Si(CH_2)_3NHC(O)(CF_2)_{14}CF_3$,
$(CH_3O)_3Si(CH_2)_3NHC(O)(CF_2)_{16}CF_3$,
$(CH_3O)_3Si(CH_2)_3NHSO_2(CF_2)_7CF_3$,
$(CH_3O)_3Si(CH_2)_3N^+(CH_3)_2(CH_2)_3NHC(O)(CH_2)_6CH_3$,
$(CH_3O)_3Si(CH_2)_3N^+(CH_3)_2(CH_2)_3NHC(O)(CH_2)_8CH_3$,
$(CH_3O)_3Si(CH_2)_3N^+(CH_3)_2(CH_2)_3NHC(O)(CH_2)_{10}CH_3$,
$(CH_3O)_3Si(CH_2)_3N^+(CH_3)_2(CH_2)_3NHC(O)(CH_2)_{12}CH_3$,
$(CH_3O)_3Si(CH_2)_3N^+(CH_3)_2(CH_2)_3NHC(O)(CH_2)_{14}CH_3$,
$(CH_3O)_3Si(CH_2)_3N^+(CH_3)_2(CH_2)_3NHC(O)(CH_2)_{16}CH_3$,
$(CH_3O)_3Si(CH_2)_3N^+(CH_3)_2(CH_2)_3NHC(O)(CF_2)_6CF_3$,
$(CH_3O)_3Si(CH_2)_3N^+(CH_3)_2(CH_2)_3NHC(O)(CF_2)_8CF_3$,
$(CH_3O)_3Si(CH_2)_3N^+(CH_3)_2(CH_2)_3NHC(O)(CF_2)_{10}CF_3$,
$(CH_3O)_3Si(CH_2)_3N^+(CH_3)_2(CH_2)_3NHC(O)(CF_2)_{12}CF_3$,
$(CH_3O)_3Si(CH_2)_3N^+(CH_3)_2(CH_2)_3NHC(O)(CF_2)_{14}CF_3$,
$(CH_3O)_3Si(CH_2)_3N^+(CH_3)_2(CH_2)_3NHC(O)(CF_2)_{16}CF_3$,
$(CH_3O)_3Si(CH_2)_3N^+(CH_3)_2(CH_2)_3NHSO_2(CF_2)_7CF_3$,
$(CH_3O)_3Si(CH_2)_3N^+(CH_3)_2(CH_2)_3NHSO_2(CF_2)_9CF_3$,
$(CH_3O)_3Si(CH_2)_3N^+(CH_3)_2(CH_2)_3NHSO_2(CF_2)_{11}CF_3$,
$(CH_3O)_3Si(CH_2)_3N^+(CH_3)_2(CH_2)_3NHSO_2(CF_2)_{13}CF_3$,
$(CH_3O)_3Si(CH_2)_3N^+(CH_3)_2(CH_2)_3NHSO_2(CF_2)_{15}CF_3$,
$(CH_3O)_3Si(CH_2)_3N^+(CH_3)_2(CH_2)_3NHSO_2(CF_2)_{16}CF_3$,
aminoethylaminopropyltrimethoxysilane: $NH_2(CH_2)_2NH(CH_2)_3Si(OCH_3)_3$,
3-aminopropyltrimethoxysilane: $NH_2(CH_2)_3Si(OCH_3)_3$,
3-aminopropyltriethoxysilane: $NH_2(CH_2)_3Si(OCH_2CH_3)_3$,
3-chloropropyltrimethoxysilane: $Cl(CU_2)_3Si(OCH_3)_3$,
3-chloropropyltriethoxysilane: $Cl(CH_2)_3Si(OCH_2CH_3)_3$,
3-chloropropyltrichlorosilane: $Cl(CH_2)_3SiCl_3$,
3-glycidoxypropyltrimethoxysilane: $C_3H_5O_2(CH_2)_3Si(OCH_3)_3$,
3-glycidoxypropyltriethoxysilane: $C_3H_5O_2(CH_2)_3Si(OCH_2CH_3)_3$,
3-methacryloxypropyltrimethoxysilane: $C_4H_5O_2(CH_2)_3Si(OCH_3)_3$,
3-methacryloxypropyltriethoxysilane: $C_4H_5O_2(CH_2)_3Si(OCH_2CH_3)_3$,
methyldichlorosilane: $CH_3SiHCl_2$,
silane-modified melamine: Dow Corning Q1-6106,
sodium (trihydroxysilyl)propylmethylphosphonate: $NaO(CH_3O)P(O)(CH_2)_3Si(OH)_3$, trichlorosilane, $SiHCl_3$,
n-2-vinylbenzylamino-ethyl-3-aminopropyltrimethoxysilane HCl: Dow Corning Z-6032,
vinyltriacetoxysilane: $H_2C=CHSi(OCOCH_3)_3$,
vinyltrimethoxysilane: $H_2C=CHSi(OCH_3)_3$,
vinyltriethoxysilane: $H_2C=CHSi(OCH_2CH_3)_3$,
vinyltrichlorosilane: $H_2C=CHSiCl_3$,
dimethyldichlorosilane: $(CH_3)_2SiCl_2$,
dimethyldimethoxysilane: $(CH_3)_2Si(OCH_3)_2$,
diphenyldichlorosilane: $(C_6H_5)_2SiCl_2$,
ethyltrichlorosilane: $(C_2H_5)SiCl_3$,
ethyltrimethoxysilane: $(C_2H_5)Si(OCH_3)_3$,
ethyltriethoxysilane: $(C_2H_5)Si(OCH_2CH_3)_3$,
isobutyltrimethoxysilane,
n-octyltriethoxysilane,
methylphenyldichlorosilane: $CH_3(Cl_6H_5)SiCl_2$,
methyltrichlorosilane: $CH_3SiCl_3$,
methyltrimethoxysilane: $CH_3Si(OCH_3)_3$,
phenyltrichlorosilane: $C_6H_5SiCl_3$,
phenyltrimethoxysilane: $C_6H_5Si(OCH_3)_3$,
n-propyltrichlorosilane: $C_3H_7SiCl_3$,
n-propyltrimethoxysilane: $C_3H_7Si(OCH_3)_3$,
silicon tetrachloride: $SiCl_4$,
$ClCH_2C_6H_4CH_2CH_2SiCl_3$,
$ClCH_2C_6H_4CH_2CH_2Si(OCH_3)_3$,
$ClCH_2C_6H_4CH_2CH_2Si(OCH_2CH_3)_3$,
decyltrichlorosilane,
dichloromethyl(4-methylphenethyl)silane,
diethoxymethylphenylsilane,
[3-(diethylamino)propyl]trimethoxysilane,
3-(dimethoxymethylsilyl)-1-propanethiol,
dimethoxymethylvinylsilane,
3-[tris(trimethylsilyloxy)silyl]propyl methacrylate,
trichloro[4-(chloromethyl)phenyl]silane,
methylbis(trimethylsilyloxy)vinylsilane,
methyltripropoxysilane, and
trichlorocyclopentylsilane.

In one particular embodiment of this invention, namely the use of the organosilane as a UV protectant, for example in a sun-tan lotion, para-amino benzoic acid is an active component. According to this embodiment of the invention, the organosilane is selected from:

$(CH_3O)_3Si(CH_2)_3NHC_6H_4COOH$
$(CH_3O)_3Si(CH_2)_3NHC_6H_4COOCH_3$
$(CH_3O)_3Si(CH_2)_3NHC_6H_4COOC_2H_5$
$(CH_3O)_3Si(CH_2)_3NHC_6H_4COOC_3H_7$
$(CH_3O)_3Si(CH_2)_3NHC_6H_4COOC_4H_9$
$(CH_3O)_3Si(CH_2)_3NHC_6H_4COOCH_2C_6H_5$
$(CH_3O)_3Si(CH_2)_3NHC_6H_4COOCH_2C_6H_4NH_2$
$(CH_3O)_3Si(CH_2)_3NHC_6H_4COOCH_2C_6H_4N(CH_3)_2$
$(CH_3O)_3Si(CH_2)_3NHC_6H_4COOCH_2C_6H_4N(CH_2CH_3)_2$
$(CH_3O)_3Si(CH_2)_3NHC_6H_4COOCH_2C_6H_4N^+(CH_3)_3Y^-$
$(CH_3O)_3Si(CH_2)_3NHC_6H_4COOCH_2C_6H_4N^+(CH_2CH_3)_3Y^-$
$(CH_3O)_3Si(CH_2)_3NCH_3C_6H_4COOH$
$(CH_3O)_3Si(CH_2)_3NCH_3C_6H_4COOCH_3$
$(CH_3O)_3Si(CH_2)_3NCH_3C_6H_4COOC_2H_5$
$(CH_3O)_3Si(CH_2)_3NCH_3C_6H_4COOC_3H_7$
$(CH_3O)_3Si(CH_2)_3NCH_3C_6H_4COOC_4H_9$
$(CH_3O)_3Si(CH_2)_3NCH_3C_6H_4COOCH_2C_6H_5$
$(CH_3O)_3Si(CH_2)_3NCH_3C_6H_4COOCH_2C_6H_4NH_2$
$(CH_3O)_3Si(CH_2)_3NCH_3C_6H_4COOCH_2C_6H_4N(CH_3)_2$
$(CH_3O)_3Si(CH_2)_3NCH_3C_6H_4COOCH_2C_6H_4N(CH_2CH_3)_2$
$(CH_3O)_3Si(CH_2)_3NCH_3C_6H_4COOCH_2C_6H_4N^+(CH_3)_3Y^-$
$(CH_3O)_3Si(CH_2)_3NCH_3C_6H_4COOCH_2C_6H_4N^+(CH_2CH_3)_3Y^-$
$(CH_3O)_3Si(CH_2)_3N^+(CH_3)_2C_6H_4COOHY^-$
$(CH_3O)_3Si(CH_2)_3N^+(CH_3)_2C_6H_4COOCH_3Y^-$
$(CH_3O)_3Si(CH_2)_3N^+(CH_3)_2C_6H_4COOC_2H_2H_5Y^-$
$(CH_3O)_3Si(CH_2)_3N^+(CH_3)_2C_6H_4COOC_3H_7Y^-$
$(CH_3O)_3Si(CH_2)_3N^+(CH_3)_2C_6H_4COOC_4H_9Y^-$
$(CH_3O)_3Si(CH_2)_3N^+(CH_3)_2C_6H_4COOCH_2C_6H_5Y^-$
$(CH_3O)_3Si(CH_2)_3N^+(CH_3)_2C_6H_4COOCH_2C_6H_4NH_2Y^-$
$(CH_3O)_3Si(CH_2)_3N^+(CH_3)_2C_6H_4COOCH_2C_6H_4N(CH_3)_2Y^-$
$(CH_3O)_3Si(CH_2)_3N^+(CH_3)_2C_6H_4COOCH_2C_6H_4N(CH_2CH_3)_2Y^-$
$(CH_3O)_3Si(CH_2)_3N^+(CH_3)_2C_6H_4COOCH_2C_6H_4N^+(CH_3)_3Y^-Y^-$
$(CH_3O)_3Si(CH_2)_3N^+(CH_3)_2C_6H_4COOCH_2C_6H_4N^+(CH_2CH_3)_3Y^-Y^-$
$(CH_3O)_3Si(CH_2)_3NC_2H_5C_6H_4COOH$
$(CH_3O)_3Si(CH_2)_3NC_2H_5C_6H_4COOCH_3$
$(CH_3O)_3Si(CH_2)_3NC_2H_5C_6H_4COOC_3H_7$
$(CH_3O)_3Si(CH_2)_3NC_2H_5C_6H_4COOC_4H_9$
$(CH_3O)_3Si(CH_2)_3NC_2H_5C_6H_4COOCH_2C_6H_5$
$(CH_3O)_3Si(CH_2)_3NC_2H_5C_6H_4COOCH_2C_6H_4NH_2$
$(CH_3O)_3Si(CH_2)_3NC_2H_5C_6H_4COOCH_2C_6H_4N(CH_3)_2$
$(CH_3O)_3Si(CH_2)_3NC_2H_5C_6H_4COOCH_2C_6H_4N(CH_2CH_3)_2$
$(CH_3O)_3Si(CH_2)_3NC_2H_5C_6H_4COOCH_2C_6H_4N^+(CH_3)_3Y^-$
$(CH_3O)_3Si(CH_2)_3NC_2H_5C_6H_4COOCH_2C_6H_4N^+(CH_2CH_3)_3Y^-$
$(CH_3O)_3Si(CH_2)_3N^+(C_2H_5)_2C_6H_4COOHY^-$
$(CH_3O)_3Si(CH_2)_3N^+(C_2H_5)_2C_6H_4COOCH_3Y^-$
$(CH_3O)_3Si(CH_2)_3N^+(C_2H_5)_2C_6H_4COOC_2H_5Y^-$
$(CH_3O)_3Si(CH_2)_3N^+(C_2H_5)_2C_6H_4COOC_3H_7Y^-$
$(CH_3O)_3Si(CH_2)_3N^+(C_2H_5)_2C_6H_4COOC_4H_9Y^-$
$(CH_3O)_3Si(CH_2)_3N^+(C_2H_5)_2C_6H_4COOCH_2C_6H_5 Y^-$
$(CH_3O)_3Si(CH_2)_3N^+(C_2H_5)_2C_6H_4COOCH_2C_6H_4N_2Y^-$
$(CH_3O)_3Si(CH_2)_3N^+(C_2H_5)_2C_6H_4COOCH_2C_6H_4N(CH_3)_2Y^-$
$(CH_3O)_3Si(CH_2)_3N^+(C_2H_5)_2C_6H_4COOCH_2C_6H_4N(CH_2CH_3)_2Y^-$
$(CH_3O)_3Si(CH_2)_3N^+(C_2H_5)_2C_6H_4COOCH_2C_6H_4N^+(CH_3)_3Y^-Y^-$
$(CH_3O)_3Si(CH_2)_3N^+(C_2H_5)_2C_6H_4COOCH_2C_6H_4N^+(CH_2CH_3)_3Y^-Y^-$
$(CH_3CH_2O)_3Si(CH_2)_3NHC_6H_4COOH$
$(CH_3CH_2O)_3Si(CH_2)_3NHC_6H_4COOCH_3$
$(CH_3CH_2O)_3Si(CH_2)_3NHC_6H_4COOC_2H_5$
$(CH_3CH_2O)_3Si(CH_2)_3NHC_6H_4COOC_3H_7$
$(CH_3CH_2O)_3Si(CH_2)_3NHC_6H_4COOC_4H_9$
$(CH_3CH_2O)_3Si(CH_2)_3NHC_6H_4COOCH_2C_6H_5$
$(CH_3CH_2O)_3Si(CH_2)_3NHC_6H_4COOCH_2C_6H_4NH_2$
$(CH_3CH_2O)_3Si(CH_2)_3NHC_6H_4COOCH_2C_6H_4N(CH_3)_2$
$(CH_3CH_2O)_3Si(CH_2)_3NHC_6H_4COOCH_2C_6H_4N(CH_2CH_3)_2$
$(CH_3CH_2O)_3Si(CH_2)_3NHC_6H_4COOCH_2C_6H_4N^+(CH_3)_3Y^-$
$(CH_3CH_2O)_3Si(CH_2)_3NHC_6H_4COOCH_2C_6H_4N^+(CH_2CH_2)_3Y^-$
$(CH_3CH_2O)_3Si(CH_2)_3NCH_3C_6H_4COOH$
$(CH_3CH_2O)_3Si(CH_2)_3NCH_3C_6H_4COOCH_3$
$(CH_3CH_2O)_3Si(CH_2)_3NCH_3C_6H_4COOC_2H_5$
$(CH_3CH_2O)_3Si(CH_2)_3NCH_3C_6H_4COOC_3H_7$
$(CH_3CH_2O)_3Si(CH_2)_3NCH_3C_6H_4COOC_4H_9$
$(CH_3CH_2O)_3Si(CH_2)_3NCH_3C_6H_4COOCH_2C_6H_5$
$(CH_3CH_2O)_3Si(CH_2)_3NCH_3C_6H_4COOCH_2C_6H_4NH_2$
$(CH_3CH_2O)_3Si(CH_2)_3NCH_3C_6H_4COOCH_2C_6H_4N(CH_3)_2$
$(CH_3CH_2O)_3Si(CH_2)_3NCH_3C_6H_4COOCH_2C_6H_4N(CH_2CH_3)_2$
$(CH_3CH_2O)_3Si(CH_2)_3NCH_3C_6H_4COOCH_2C_6H_4N^+(CH_3)_3Y^-$
$(CH_3CH_2O)_3Si(CH_2)_3NCH_3C_6H_4COOCH_2C_6H_4N^+(CH_2CH_3)_3Y^-$
$(CH_3CH_2O)_3Si(CH_2)_3N^+(CH_3)_2C_6H_4COOHY^-$
$(CH_3CH_2O)_3Si(CH_2)_3N^+(CH_3)_2C_6H_4COOCH_3Y^-$ $(CH_3CH_2O)_3Si(CH_2)_3N^+(CH_3)_2C_6H_4COOC_2H_5Y^-$
$(CH_3CH_2O)_3Si(CH_2)_3N^+(CH_3)_2C_6H_4COOC_3H_7Y^-$
$(CH_3CH_2O)_3Si(CH_2)_3N^+(CH_3)_2C_6H_4COOC_4H_9Y^-$
$(CH_3CH_2O)_3Si(CH_2)_3N^+(CH_3)_2C_6H_4COOCH_2C_6H_5\ Y^-$
$(CH_3CH_2O)_3Si(CH_2)_3N^+(CH_3)_2C_6H_4COOCH_2C_6H_4NH_2Y^-$
$(CH_3CH_2O)_3Si(CH_2)_3N^+(CH_3)_2C_6H_4COOCH_2C_6H_4N(CH_3)_2Y^-$
$(CH_3CH_2O)_3Si(CH_2)_3N^+(CH_3)_2C_6H_4COOCH_2C_6H_4N(CH_2CH_3)_2Y^-$
$(CH_3CH_2O)_3Si(CH_2)_3N^+(CH_3)_2C_6H_4COOCH_2C_6H_4N^+(CH_3)_3Y^-Y^-$
$(CH_3CH_2O)_3Si(CH_2)_3N^+(CH_3)_2C_6H_4COOCH_2C_6H_4N^+(CH_2CH_3)_3Y^-Y^-$
$(CH_3CH_2O)_3Si(CH_2)_3NC_2H_5C_6H_4COOH$
$(CH_3CH_2O)_3Si(CH_2)_3NC_2H_5C_6H_4COOCH_3$
$(CH_3CH_2O)_3Si(CH_2)_3NC_2H_5C_6H_4COOC_2H_5$
$(CH_3CH_2O)_3Si(CH_2)_3NC_2H_5C_6H_4COOC_3H_7$
$(CH_3CH_2O)_3Si(CH_2)_3NC_2H_5C_6H_4COOC_4H_9$
$(CH_3CH_2O)_3Si(CH_2)_3NC_2H_5C_6H_4COOCH_2C_6H_5$
$(CH_3CH_2O)_3Si(CH_2)_3NC_2H_5C_6H_4COOCH_2C_6H_4NH_2$
$(CH_3CH_2O)_3Si(CH_2)_3NC_2H_5C_6H_4COOCH_2C_6H_4N(CH_3)_2$
$(CH_3CH_2O)_3Si(CH_2)_3NC_2H_5C_6H_4COOCH_2C_6H_4N(CH_2CH_3)_2$
$(CH_3CH_2O)_3Si(CH_2)_3NC_2H_5C_6H_4COOCH_2C_6H_4N^+(CH_3)_3Y^-$
$(CH_3CH_2O)_3Si(CH_2)_3NC_2H_5C_6H_4COOCH_2C_6H_4N^+(CH_2CH_3)_3Y^-$
$(CH_3CH_2O)_3Si(CH_2)_3N^+(C_2H_5)_2C_6H_4COOHY^-$
$(CH_3CH_2O)_3Si(CH_2)_3N^+(C_2H_5)_2C_6H_4COOCH_3Y^-$
$(CH_3CH_2O)_3Si(CH_2)_3N^+(C_2H_5)_2C_6H_4COOC_2H_5Y^-$
$(CH_3CH_2O)_3Si(CH_2)_3N^+(C_2H_5)_2C_6H_4COOC_3H_7Y^-$
$(CH_3CH_2O)_3Si(CH_2)_3N^+(C_2H_5)_2C_6H_4COOC_4H_9Y^-$
$(CH_3CH_2O)_3Si(CH_2)_3N^+(C_2H_5)_2C_6H_4COOCH_2C_6H_5Y^-$
$(CH_3CH_2O)_3Si(CH_2)_3N^+(C_2H_5)_2C_6H_4COOCH_2C_6H_4NH_2Y^-$
$(CH_3CH_2O)_3Si(CH_2)_3N^+(C_2H_5)_2C_6H_4COOCH_2C_6H_4N(CH_3)_2Y^-$
$(CH_3CH_2O)_3Si(CH_2)_3N^+(C_2H_5)_2C_6H_4COOCH_2C_6H_4N(CH_2CH_3)_2Y^-$
$(CH_3CH_2O)_3Si(CH_2)_3N^+(C_2H_5)_2C_6H_4COOCH_2C_6H_4N^+(CH_3)_3Y^-Y^-$, and
$(CH_3CH_2O)_3Si(CH_2)_3N^+(C_2H_5)_2C_6H_4COOCH_2C_6H_4N^+(CH_2CH_3)_3Y^-Y^-$.

Stabilizers

As described herein, preferred stabilizers of the present invention preferably contain at least two hydroxy groups, where at least two of said at least two hydroxy groups are separated by less than three intervening atoms, i.e., (HO—A—B—OH where A and B are any one or two atoms). Such stabilizers can stabilize aqueous solutions of the above-described organosilanes $R_nSiX_{4-n}$ and are generally useful for stabilization of all such solutions where n is an integer from 0 to 2 and where water solubility or minimization or prevention of water-induced, self-condensation (and associated polymerization) is desired. In particular, preferred stabilizers are monosaccharides, including but not limited to glucose, disaccharides, including but not limited to sucrose, polysaccharides, polynucleotides, and alcohols, wherein at least two adjacent hydroxyls separated by fewer than three intervening atoms are present in the stabilizer.

Uses

The compounds, products and compositions of the present invention are useful for a multitude of purposes. Such purposes include any known use for the preferred starting material organosilanes of the above-described general formula. In preferred embodiments, the presently described, water-stabilized, organosilane compounds, products and compositions are suitable to applications such as: 1) treatment of surfaces, including fillers and pigments, 2) additives to coatings such as dyes, or 3) as additives to organic monomers (such as acrylics) prior to formation of the respective polymer.

Therefore, in addition to the utility of prior organosilane quaternary ammonium compounds such as 3-(trimethoxysilyl)propyl-dimethyloctadecyl ammonium chloride as surface bonding antimicrobial agents, numerous other uses of organofunctional silanes are contemplated, such as the use of the compounds, products and compositions of the invention in coating applications which include the treatment of surfaces or particles (pigments or fillers), in primers, in paints, inks, dyes and adhesives, and as reactive intermediates for silicone resin synthesis.

The present invention can be used to prepare, inter alia, agricultural products, cleaning compositions, antimicrobial sponges, antimicrobial bleaching agents, antimicrobial fillers for paints, plastics, or concrete, and to treat concrete structures such as livestock shelters, where microbial infestation is a problem.

In various embodiments, surfaces and substrates treatable with the compounds, products and compositions of the invention solution include, but are not limited to, textiles, carpet, carpet backing, upholstery, clothing, sponges, plastics, metals, surgical dressings, masonry, silica, sand, alumina, aluminum chlorohydrate, titanium dioxide, calcium carbonate, wood, glass beads, containers, tiles, floors, curtains, marine products, tents, backpacks, roofing, siding, fencing, trim, insulation, wall-board, trash receptacles, outdoor gear, water purification systems, and soil. Furthermore, articles treatable with the compounds, products and compositions of the invention include, but are not limited to, air filters and materials used for the manufacture thereof, aquarium filters, buffer pads, fiberfill for upholstery, fiberglass ductbdard, underwear and outerwear apparel, polyurethane and polyethylene foam, sand bags, tarpaulins, sails, ropes, shoes, socks, towels, disposal wipes, hosiery and intimate apparel; cosmetics, lotions, creams, ointments, disinfectant sanitizers, wood preservatives, plastics, adhesives, paints, pulp, paper, cooling water, and laundry additives and non-food or food contacting surfaces in general.

For the above described substrates, mixtures and applications, treatment generally involves contacting or mixing the article to be treated with a water-stabilized organosilane solution of the present invention, comprising the organosilane-stabilizer derived compound in an aqueous solution, for a period of time sufficient for permanent bonding of the active organosilane ingredient (or portion thereof) to the article. Generally, treatment begins almost immediately upon contact, but preferably requires from about 15 seconds to about 48 hours, more preferably from about 1 minutes to about 24 hours, even more preferably from about five minutes to 1 hour, and even more preferably for about 30 minutes. Further general guidelines for application are as follows: For dipping a large object, it is preferred that 1–2 minutes of submersion is allowed in the solution and then the object is permitted to dry or is dried. However, some objects will benefit from very short dipping, mixing or contacting times, for example, fabric may pass through an aqueous bath of the composition at a rate of up to 40 yards per minute or more. After dipping, excess solution may be gently wiped or rinsed off. Alternatively, the solution may be sprayed on the substrate. Moreover, the composition of the invention may be placed in a high intensity solid mixer and formed into a powder which is then dried. The dried powder may then be used in a sprayer, if desired. In addition, the solutions may be wiped onto the substrate and applied using sponges or cloths, etc. Moreover, the solutions of the present invention can be added to pigments and fillers and stirred therewith for several (2–3) minutes. In addition, the solutions can be added to an emulsion or other existing formulation prior to use. Also, the solutions can be used in addition to, with or as a spray coolant for extruded fibers. However, one of ordinary skill in the art would recognize that numerous other uses and modes of application are readily apparent from the stabilized organosilane compounds, products and compositions of the present invention and would, without undue experimentation, be able to determine effective application methods and treating times for any particular substrate, article, or other application. In addition, the compositions can be used in padding processes as are known in textile mills.

Moreover, after treating. a surface or fabric with the compound, product or compositions of the present invention, the surface or fabric may, optionally, be heated to further complete bonding of the compound, product, or composition to the surface or substrate.

The water-stable organosilane compounds, products and compositions of the present invention are, therefore, advantageous in treating a variety of substrates without the use of toxic organic solvents, and provide for the safe, long-term storage of activated organosilane compound which can be used without further preparation. Moreover, the stabilizers described herein do not interfere with the binding of the organosilane to the substrate. In addition, the present invention provides a generally applicable scheme for solvating some water insoluble organosilanes.

Also apparent will be those applications where organosilanes $R_nSiX_{4-n}$ are prepared, dissolved, stored, applied, and in any way used in water. In addition, also apparent will be those applications of organosilanes $R_nSiX_{4-n}$, in other solvents or mixed in other media (solids, polymer mixes, fillers, pigments, powders, dyes or emulsions) where exposure to water occurs but could be detrimental due to undesired or untimely self-condensation of the silanol.

Moreover, the stabilizing compounds and methods could be used in addition to or in conjunction with various art-known stabilization methods for organosilanes, such as the use of ionic or non-ionic surfactants and detergents.

In addition, it is believed that the compounds, products and compositions of the present invention lead to improved wetting and/or coating because the partially hydrolyzed stabilizer/organosilane complex is dense in hydroxyl groups, thus providing for increased hydrogen-bonding to surface OH groups.

Moreover, the present compounds, products and compositions can be used in the incorporation of an organosilane antimicrobial agent in most textile goods (woven and non-woven) and yarns (synthetic and natural). The process provides articles that are durable and the process itself is effective and does not require additional manufacturing steps or increase manufacturing cost.

Incorporating the compounds, products and compositions of the present invention during the dye process yields a textile material with a built-in antimicrobial agent with the organosilane characteristics, binding and antimicrobial protection. The incorporation process 1) does not add any additional step in the manufacturing process and does not require any equipment modification; and 2) is believed not to lose its antimicrobial characteristics and its effectiveness during further production of the textile goods. By incorporating the water-stable compounds, products and compositions of the present invention during the dye process, not only would the organosilane antimicrobial agent remain unaffected by the dying agent, but the end-product textile goods would also exhibit excellent dyeing properties.

The water-stabilized organosilane compounds, products and compositions of the present invention are useful for a number of applications where the previous instability, insolubility prevented or, at least, hindered or restricted use of some organosilane agents.

For example:

Treating food crops (e.g., perishables such as vegetables, fruits, or grains) after removal (pickled/harvested) with the compounds, products and compositions of the present invention imparts antimicrobial protection to the outer surface of the food crop. It is believed that such protection occurs without diffusing, migrating or leaching the antimicrobial agent from the bonded antimicrobial coating of the food item, and provides prolonged, safe and non-toxic antimicrobial protection. The method involves treating fruits and vegetables in the rinse cycle, during or after the normal cleaning/water spraying or during or after blanching. Thorough cleaning of fruits and vegetables at the processing plant is preferred for initially removing microorganisms. As one of ordinary skill in the art would recognize, machines are used initially to remove soil, chemicals used in growing, spoilage bacteria, and other foreign materials. These machines also use high velocity water sprays to clean the products. After the cleaning, raw foods or other crop materials are prepared for further processing such as blanching (i.e., the food is immersed in water at 190 to 210 degrees F. or exposed to steam).

Microorganisms are controlled by the production plant up until the fruit or vegetable is removed. But once it is removed, organisms such as yeast, mold, and bacteria, begin to multiply, causing the food to loose flavor and change in color and texture. To keep the food from spoiling, a number of methods have been employed, such as refrigerators, to slow down the microorganisms and delay deterioration. Unfortunately, such known methods will preserve raw foods for few weeks at the most. The compounds, products and compositions of the present invention can preserve these items for extended periods. For instance, the compositions, products, or compounds may be added to an existing water line feeding the sprayers for the foods, where such sprayers are used. Otherwise, a simple dipping process may be used, where the dipping requires only a few seconds to impart antimicrobial protection. Low concentrations of 0.1 to 1% aqueous solution (0.1 to 1% by volume) of the compositions provide satisfactory results. In addition, it is believed that the presently described method can also control pathogens on poultry carcasses and in other susceptible meat and fish.

Treating Baby Milk/Juice Bottles, Nipples, Pacifiers and Toys with the compounds, products and compositions of the present invention in the factory or leaching the agent from the bonded surface, can provide prolonged and safe/non-toxic antimicrobial protection. Treating such articles also eliminates odors caused by microbial contamination. A dipping method as described above may be used to treat these articles.

To date, parents have used soaps, detergents, and surface cleaners to alleviate the problems of contamination of these articles. However, these and other similar treatments have, for the most part, been inadequate and required repeated treatment. In addition, these treatments have been found to be limited in their ability to offer broad spectrum control of microorganisms. Therefore, the present compounds, products and compositions can be used to treat these articles to prevent microbial growth and contamination by coating an effective amount of the products and compounds of the invention thereon. The articles employed can be coated by allowing for 1 to 2 minutes submersion (e.g., by dipping), and thereafter, the treated surface is allowed to dry at room temperature. The article is then rinsed of any excess antimicrobial agent. Thorough cleaning and sterilization is a preferred step in removing the microorganismson the surface of the article prior to "coating" the said articles. In addition, preferably concentrations of 10% or more by volume of the compounds, products and compositions of the invention are used for long lasting protection.

Treating surgical gloves with the compounds, products and compositions of the present invention before or during a surgical procedure can kill microorganisms on contact. It is believed that the treated gloves provide prolonged antimicrobial activity with safe and non-toxic antimicrobial protection. Surgical gloves are treated, preferably, by submerging in the solution of Example I, diluted to 1% W/V for at least 30 seconds. This method will permit doctors to use and, if necessary, re-use the same gloves (even without removing them) without undue fear of contamination.

Moreover, one of ordinary skill in the art would be able to implement numerous other end uses based upon the disclosure of the compounds, products and compositions of the present invention. For instance, the following uses, applications and substrates, are contemplated:

1. Concrete, Concrete Water Conduits, Storm and Sewer Pipes treated with the compounds, products and compositions of the present invention. Agents to kill microorganism on contact and provide prolonged antimicrobial protection to prevent deterioration of the concrete and its coatings;
2. Tooth Brushes, Combs, Hair Brushes, Dentures and Retainers;
3. Spa and Pool Filters meeting stringent requirements that no other antimicrobial agent can meet and protection for Air Filtration such as air conditioning filters, HVAC applications and cabin air;
4. Marble Slabs (building facia, tombs, floors) treated with the compounds, products and compositions of the present invention;
5. Rubbing Alcohol;
6. Statues and exposed art work;
7. HDP, high density polyester fabric plastic covers for dump sites, water reservoirs and generally for soil protection;
8. Liquid Additive (as flower water preservative for potted plants and cut flowers);
9. Silicone and Teflon coated Fiberglass with antimicrobial protection including acrylic backing wall covering;
10. Dryvitt and Stucco finish;
11. Waterproofing treated with the compounds, products and compositions of the present invention;
12. A method of treating blended cotton before or after picking machines make the cotton into rolls or laps;
13. Food packaging and containers;
14. Bio-films and adhesives (tapes and silicone wafers);
15. Single Ply Roofing and Roof shingles;
16. Fiberglass reinforcement product;
17. Antimicrobial treatment of a transplant;
18. Antimicrobial treatment of an organ or cartilage transplant;
19. Antimicrobial treatment of an artificial transplant such as a replacement bone;
20. Antimicrobial treatment of a skin transplant, artificial, not artificial or a mixture of both;
21. Treatment of a transplant to reduce rejection by the receiving organism;
22. Treatment of a skin transplant;
23. Treatment of a transplant to reduce undesired deposits, especially for artificial transplants;
24. Treatment to accelerate the attachment of natural bone to non-organ transplants;
25. Preservation of liquids for consumption without pasteurization and nutrient reduction;
26. Skin treatment not incorporating any water insoluble materials to stabilize siloxane;
27. Timed drug delivery, based on hydrolysis of siloxane attached to areas of activity;
28. Throat lozenges providing relief and microbial kill;
29. Treatment of contact lenses to prevent or slow down deposit formation;
30. Treatment of contact lenses to prevent microbial growth;
31. Incorporation into commercial polymers to render them antimicrobially active and/or prevent damage by microbial growth on surface. Examples of the commercial polymers are polyester, polyamide (nylon), polyvinyl chloride, polyethylene, polypropylene, polystyrene, polyurethane, plyvinyl alcohol, polyformaldehyde;
32. Incorporation into contact lenses to achieve the results as noted above in items 28 and 29 for the long term and without additional surface treatment;
33. Incorporation into polyester to provide food containers with antimicrobial properties without separate surface treatment;
34. Incorporation into polypropylene or polyethylene to provide food containers with antimicrobial properties without separate surface treatment;
35. Incorporation of siloxane into CD-Rom to reduce the effect of microbes growing on surface;
36. Treatment of paper (newspaper, books, documents) to prevent aging such as yellowing and weakening of material;
37. Effective cleaning and odor prevention in animal cages, i.e. birds, hamster, pigs, guinea pigs, horses, cattle, rats and mice;
38. Disinfecting in spacecrafts, low vapor pressure and no irritation of astronauts by cleaner but high residual activity;
39. Applications in clean rooms, i.e. clean-rooms used in the microprocessor industries, reduction of harmful effects of microbes and uses as a binder for dust, and inhibitor of static charge;
40. Application of a non-conducting layer over circuit boards to prevent damage from dust and other atmospheric pollutants;
41. Application of a durable, non irritating UV-protector for polymers, skin, leather, and wood;
42. The UV-protector can be formulated for example in a sun tan lotion or for example with lubricants to protect polymers such as dash boards and car tires;
43. Protection of photographic products from microbials, such as lenses, photographs, film and solutions used in film development;

44. Protection of photographic products, such as lenses, photographs, film and solutions used in film development from static and dirt;
45. Protection of photographic products from stains and scratching, such as lenses, photographs, film and solutions used in film development;
46. Protective coating for microchips;
47. Use of self assembled layers in designing and manufacturing microchips;
48. Use of self assembled layers in wiring of microchips;
49. Use of self assembled layers in manufacturing molecular processors;
50. Additive to dryer sheets to render clothes antimicrobially active;
51. Aid in wound closing and healing and prevention of wound infection;
52. Treatment of nail fungus for example by addition to nail polish.

It will be appreciated by those skilled in the art, in view of what is disclosed herein, that the compositions of this invention are useful, independent of the mechanism of operation, which may or may not include the hydrolysis of siloxane to silanol and possible reaction of the silanol with the polyol, or alternatively, mere stabilization of the siloxane by interaction with the polyol, for example, by hydrogen bonding. It will also be understood that where a composition is recited as containing an organosilane, mixtures of organosilanes is also intended and encompassed thereby.

In particularly preferred embodiments, the composition according to this invention is used to treat skin or other tissues (bone, soft tissues) for use in a transplant to reduce microbial contamination. The composition is likewise useful in any toothpaste formulation known in the art to enhance the caries-fighting properties of such compositions through anti-microbial treatment of teeth.

In other preferred embodiments, the composition is used to protect paper products,, to produce dural metal finishes, such as any car wax formulation known in the art, to prevent paint scratches and as a protectant against the accumulation of dirt.

The preferred embodiments of the above-described water-stabilized antimicrobial compounds, products, compositions, and methods are set forth in the following examples. Other features of the invention will become apparent from the following examples, which are for illustrative purposes only and are not intended as a limitation upon the present invention.

EXAMPLE 1

In one embodiment, the present invention provides a water-stable composition of glucose and a silylated quaternary ammonium salt. Upon application of the mixture, the glucose is most likely partially liberated and the product is hydrolyzed. However, such liberation is not necessary for the operability of the present invention. Its occurrence or non-occurrence does not detract from the general efficacy of the compounds, products and compositions of the present invention. Instead, the notion that glucose (or any other of the present stabilizers) is liberated is offered as one possible explanation of the surprising utility and efficacy of the claimed invention. It is not clear that the stabilizer must be liberated when the organosilane bonds to a substrate.

Glucose stabilized 3-(trimethoxysilyl) propyldimethyloctadecyl ammonium chloride is stable in water up to concentrations of 10% W/W of the siloxane. One of ordinary skill in the art would recognize that the stability of other organosilanes may vary and depends upon the specific stabilizer used. In any event, the siloxane and the glucose are mixed, optionally at a higher final siloxane concentration than the working concentration, and then diluted to the desired active concentration in water.

EXAMPLE 2

Compositions wherein the stabilization of the siloxane is achieved through mixing with sucrose is similar to that described in Example 1 for stabilization with glucose.

EXAMPLE 3

A series of polyols were tested for their ability to stabilize Dow Corning 5772, which is a blend of [3-(trimethoxysilyl) propyldimethyloctadecyl ammonium chloride], and 3-chloropropyltrimethoxysilane, aqueous solutions and the degree of stabilization over various time periods was monitored. In general, most concentrations of siloxane become cloudy overnight in the absence of stabilizer. Therefore, when aqueous siloxanes remain stable overnight in the presence of stabilizer, the polyol is considered to have at least minimal utility according to this invention. However, those skilled in the art will recognize that for practicality and commercial applications, the longer the period for which a stable composition can be achieved the better. Accordingly, a stock of solutions of known concentrations of the stabilizer is prepared in deionized water. A known amount of the solution, and in some cases additional deionized water and the siloxane were mixed in a vial. The vial was sealed with parafilm to prevent evaporation, and stored at ambient temperature. The percent antimicrobially active siloxane was calculated by multiplying the weight of Dow Corning 5772 added by 0.72 and dividing by the sum of all materials added (polyol, Dow Corning 5772, deionized water). We found that for at least 10% or lower siloxane concentrations, about 1–20% of the polyol was effective at stabilizing the aqueous solution.

EXAMPLE 4

A 5% siloxane solution with 0.94% to 19% sucrose remained clear for at least seven weeks. Another sample at approximately 5% active siloxane remained clear for at least eight months.

EXAMPLE 5

A 5% siloxane solution with 0.94% to 19% mannitol remained clear for seven weeks. At the high mannitol concentration, the mannitol is not completely soluble, but still active as a stabilizer of the siloxane.

EXAMPLE 6

A 5% siloxane solution with 0.94% to 19% glucose remained clear for at least eight weeks.

EXAMPLE 7

A 10% siloxane solution with 0.85% to 17% L-ascorbic acid remained clear for at least five weeks; after two days, solutions with as much as 18% siloxane remained clear with as little as 0.79% L-ascorbic acid.

EXAMPLE 8

A 9% siloxane, with 4.1% to 18% glyoxal aqueous solution remained clear for at least three weeks.

EXAMPLE 9

In terms of polymeric polyols, we found that a 5% siloxane, 0.097% agar solution was stable for at least one week. As will be appreciated, for agar, it is necessary to warm the stock agar solution to achieve dissolution of the agar, which is then cooled prior to or in the course of admixture with the siloxane. The resulting solution is a viscous liquid or solid when cold.

EXAMPLE 10

In terms of an oxidized sugar, we found that a 9.7% siloxane, 0.9% D-glucurono-6,3-lactone aqueous solution was stable for at least four weeks.

EXAMPLE 11

A tannic acid siloxane solution was not stabilized to any significant degree. This result may indicate that impurities, for example oxidation products, in the tannic acid may have inhibited its action as a stabilizer. Alternatively, the limited stabilization afforded by tannic acid may indicate that at least two adjacent (separated by less than three atoms) hydroxyls of the stabilizer are, preferably non-aromatic.

EXAMPLE 12

According to this invention, a number of compositions comprising mixtures of siloxanes and polyols may be, contemplated for a wide variety of applications. Because stabilizers of this invention include such non-toxic, biocompatible substances as simple sugars and more complex carbohydrates, compositions such as shampoos, hand and face creams, and compositions that come in contact with foods are all acceptable applications. There are many compositions known in the art for these types of applications, to which those skilled in the art could apply the instant disclosure, and therefore great detail on the various components of those compositions is not provided herein. Thus, shampoo, hand-lotion, tooth-paste, and other biological material contacting compositions known in the art may include the composition according to this invention. However, such biologically contacting compositions are by no means the only useful compositions. Other compositions known in the art, such as car wax, furniture polish, shoe polish, leather treatment compositions, or glass treatment compositions are improved by the inclusion of the composition according to this invention.

From the foregoing examples, those skilled in the art will recognize that the stabilizers disclosed herein may be used at any minimal concentration at which they are found to have a stabilizing effect, and may be used up to any maximum concentration at which they remain soluble. Even where some amount of solid stabilizer is present, this is not expected to have any deleterious effect, (see the above experiment in which a high mannitol concentration was used), although it is anticipated that in terms of siloxane stabilization, a point of diminishing returns is reached where increased concentrations of stabilizer do not yield commensurate enhancements in siloxane stabilization.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A composition comprising a mixture of:
   a) an organosilane of the formula $R_nSiX_{4-n}$ where n is an integer of from 0 to 3; and R is, independently, a nonhydrolizable organic group; and each X is, independently, a hydrolyzable group; with
   b) a polyol selected from the group consisting of
      (i) glucose, sucrose, fructose, mannitol, ascorbic acid and optionally including an anti-oxidant, adenosine, glucuronic acid, glucurone, dextrose, cellulose, partially hydrolyzed cellulose, soluble starch, a starch-acrylic acid graft copolymer, a nucleoside, a nucleotide, an oligonucleotide, or a polynucleotide;
      (ii) an aldose, ketose, or aldose or ketose oxidized or reduced in a single step;
      (iii) substituted aldose, substituted ketose, or substituted aldose or substituted ketose oxidized or reduced in a single step;
      (iv) a polymer of aldose, a polymer of ketose, a polymer of aldose and ketose, or any thereof oxidized or reduced in a single step; and
      (v) a substituted polymer of aldose, a substituted polymer of ketose, a substituted polymer of aldose and ketose, or any thereof oxidized or reduced in a single step; and
   c) water;

wherein said organosilane amounts to about 20% or less by weight of said composition.

2. The composition of claim 1, wherein the organosilane is of the formula II, III, IV, or V:

$(R_1)_3SiR_2N^+(R_3)(R_4)(R_5)Y^-$ (II)

$(R_1)_3SiR_2N(R_3)(R_4)$ (III)

$(R_1)_3SiR_2R_{35}$ (IV)

$(R_1)_2Si(R_{36})(R_{37})$ (V)

wherein
   each $R_1$ is, independently, halogen or $R_6O$, where $R_6$ is H, alkyl of from 1 to about 22 carbon atoms, acetyl, acetoxy, acyl, propylene glycol, ethylene glycol, polyethylene glycol, polypropylene glycol; block and copolymers of ethylene and propylene glycol, the alkyl monoether of from 1 to 22 carbons of propylene glycol, ethylene glycol, polyethylene glycol, polypropylene glycol; block and copolymers of ethylene and propylene glycol or the monoester of a carbonic acid of from 1 to 22 carbons and propylene glycol, ethylene glycol, polyethylene glycol, polypropylene glycol; block and copolymers of ethylene and propylene glycol; octyphenol; nonylphenol;1 or sorbitan ethers;
   $R_{35}$ is H, halogen, $NH_2(CH_2)_2NH$, $NH_2$, $C_3H_5O_2$, $C_4H_5O_2$, $NaO(CH_3O)P(O)$, or $ClCH_2C_6H_4$,
   $R_{36}$ and $R_{37}$ are, independently, halogen, H, alkyl of from 1 to about 22 carbon atoms, acrylic, vinyl, acetylenic, benzyl, styryl, propinyl, isobutyl, phenyl, or n-octyl;
   $R_2$ is benzyl, vinyl or alkyl of from 1 to about 22 carbon atoms;
   $R_3$ and $R_4$ are, independently, lower alkyl alcohol, lower alkoxy of from 1 to 4 carbon atoms, alkyl of from 1 to about 22 carbon atoms; or $R_3$ and $R_4$ can, together, form a morpholine or cyclic or heterocyclic, unsaturated or saturated, five to seven-membered ring of the formula VI:

$-R_3-(R_7)_k-R_4-$ (VI)

where
k is an integer from 0 to 2,
R$_7$, where the ring is saturated, is CH$_2$, O, S, NH, NH$_2$$^+$, NCH$_2$CH$_2$NH$_2$, NCH$_2$CH$_2$NH$_3$$^+$, NCH$_2$CH$_2$N(R$_8$)(R$_9$), NCH$_2$CH$_2$N$^+$(R$_8$)(R$_9$) (R$_{10}$), N(alkyl), N(aryl), N(benzyl), where each R$_8$, R$_9$, and R$_{10}$ is, independently, benzyl, polyether, lower alkyl alcohol of from 1 to 4 carbon atoms, lower alkoxy of from 1 to 4 carbon atoms, or alkyl of from 1 to about 22 carbon atoms, and R$_7$, where the ring is unsaturated is, CH, N, N$^+$H, N$^+$(alkyl), N$^+$(aryl), N$^+$(benzyl), N—CH$_2$—N, N$^+$H—CH$_2$—N, N$^+$(alkyl)-CH$_2$—N, N$^+$(aryl)-CH$_2$—N, or N$^+$(benzyl)-CH$_2$—N; wherein the ring is unsubstituted or substituted with alkyl of from 1 to 22 carbon atoms, ester, aldehyde, carboxylate, amide, thionamide, nitro, amine, or halide;

R$_5$ is lower alkyl alcohol, CH$_2$C$_6$H$_5$, polyether, alkyl, alkoxy, perfluoroalkyl, pefluoroalkylsulfonate, or perfluoroalkylcarboxylate wherein the alkyl, alkoxy, perfluoroalkyl, perfluoroalkylsulfonate, or perfluoroalkylcarboxylate is of from 1 to about 22 carbon atoms, or is a five to seven-membered ring of formula VI as described above; and Y is a suitable anionic moiety to form the salt of the compound of formula II, III, IV or V.

3. The composition of claim 1, wherein the organosilane is (CH$_3$O)$_3$Si(CH$_2$)$_3$N$^+$(CH$_3$)$_2$C$_{18}$H$_{37}$Cl$^-$, (CH$_3$O)$_3$Si(CH$_2$)$_3$N$^+$(CH$_3$)$_2$C$_{18}$H$_{37}$BR$^-$,
(CH$_3$O)$_3$Si(CH$_2$)$_3$N$^+$(C$_{10}$H$_{21}$)$_2$CH$_3$Cl$^-$, (CH$_3$O)$_3$Si(CH$_2$)$_3$N$^+$(C$_{10}$H$_{21}$)$_2$CH$_3$BR$^-$,
(CH$_3$O)$_3$Si(CH$_2$)$_3$N$^+$(CH$_3$)$_3$Cl$^-$, (CH$_3$)$_3$Si(CH$_2$)$_3$N$^+$(CH$_3$)$_2$C$_8$H$_{17}$Cl$^-$,
(CH$_3$O)$_3$Si(CH$_2$)$_3$N$^+$(CH$_3$)$_2$C$_{10}$C$_{21}$Cl$^-$, (CH$^{30}$)$_3$Si(CH$_2$)$_3$N$^+$(CH$_3$)$_2$C$_{12}$H$_{25}$Cl$^-$,
(CH$_3$O)$_3$Si(CH$_2$)$_3$N$^+$(CH$_3$)$_2$C$_{14}$H$_{29}$Cl$^-$, (CH$_3$)$_3$Si(CH$_2$)$_3$N$^+$(CH$_3$)$_2$C$_{16}$H$_{33}$Cl$^-$,
(CH$_3$O)$_3$Si(CH$_2$)$_3$N$^+$(CH$_3$)$_2$C$_{20}$H$_{41}$Cl$^-$, (CH$_3$)$_3$Si(CH$_2$)$_3$N$^+$(C$_4$H$_9$)$_3$Cl$^-$,
(CH$_3$O)$_3$Si(CH$_2$)$_3$N$^+$(C$_2$H$_5$)$_3$Cl$^-$, (CH$_3$CH$_2$)$_3$Si(CH$_2$)$_3$N$^+$(CH$_3$)$_2$C$_{18}$H$_{37}$Cl$^-$,
(CH$_3$O)$_3$Si(CH$_2$)$_3$NHC(O)(CF$_2$)$_6$CF$_3$, (CH$_3$O)$_3$Si(CH$_2$)$_3$NHC(O)(CF$_2$)$_8$CF$_3$,
(CH$_3$O)$_3$Si(CH$_2$)$_3$NHC(O)(CF$_2$)$_{10}$CF$_3$, (CH$_3$O)$_3$Si(CH$_2$)$_3$NHC(O)(CF$_2$)$_{12}$CF$_3$,
(CH$_3$O)Si(CH$_2$)$_3$NHC(O)(CF$_2$)$_{14}$CF$_3$, (CH$_3$O)$_3$Si(CH$_2$)$_3$NHC(O)(CF$_2$)$_{16}$CF$_3$,
(CH$_3$O)$_3$Si(CH$_2$)$_3$NHSO$_2$(CF$_2$)$_7$CF$_3$,
(CH$_3$O)$_3$Si(CH$_2$)$_3$N$^+$(CH$_3$)$_2$(CH$_2$)$_3$NHC(O)(CH$_2$)$_6$CH$_3$,
(CH$_3$O)$_3$Si(CH$_2$)$_3$N$^+$(CH$_3$)$_2$(CH$_2$)$_3$NHC(O)(CH$_2$)$_8$CH$_3$,
(CH$_3$O)$_3$Si(CH$_2$)$_3$N$^+$(CH$_3$)$_2$(CH$_2$)$_3$NHC(O)(CH$_2$)$_{10}$CH$_3$,
(CH$_3$O)$_3$Si(CH$_2$)$_3$N$^+$(CH$_3$)$_2$(CH$_2$)$_3$NHC(O)(CH$_2$)$_{12}$CH$_3$,
CH$_3$O)$_3$Si(CH$_2$)$_3$N$^+$(CH$_3$)$_2$(CH$_2$)$_3$NHC(O)(CH$_2$)$_{14}$CH$_3$,
(CH$_3$O)$_3$Si(CH$_2$)$_3$N$^+$(CH$_3$)$_2$(CH$_2$)$_3$NHC(O)(CH$_2$)$_{16}$CH$_3$,
(CH$_3$O)$_3$Si(CH$_2$)$_3$N$^+$(CH$_3$)$_2$(CH$_2$)(CH$_2$)$_3$NHC(O)(CF$_2$)$_6$CF$_3$,
(CH$_3$O)$_3$Si(CH$_2$)$_3$N$^+$(CH$_3$)$_2$(CH$_2$)$_3$NHC(O)(CF$_2$)$_8$CF$_3$,
(CH$_3$O)$_3$Si(CH$_2$)$_3$N$^+$(CH$_3$)$_2$(CH$_2$)$_3$NHC(O)(CF$_2$)$_{10}$CF$_3$,
(CH$_3$O)$_3$Si(CH$_2$)$_3$N$^+$(CH$_3$)$_2$(CH$_2$)$_3$NHC(O)(CF$_2$)$_{12}$CF$_3$,
(CH$_3$O)$_3$Si(CH$_2$)$_3$N$^+$(CH$_3$)$_2$(CH$_2$)$_3$NHC(O)(CF$_2$)$_{14}$CF$_3$,
(CH$_3$O)$_3$Si(CH$_2$)$_3$N$^+$(CH$_3$)$_2$(CH$_2$)$_3$NHC(O)(CF$_2$)$_{16}$CF$_3$,
(CH$_3$O)$_3$Si(CH$_2$)$_3$N$^+$(CH$_3$)$_2$(CH$_2$)$_3$NHSO$_2$(CF$_2$)$_7$CF$_3$,
(CH$_3$O)$_3$Si(CH$_2$)$_3$N$^+$(CH$_3$)$_2$(CH$_2$)$_3$NHSO$_2$(CF$_2$)$_9$CF$_3$,
(CH$_3$O)$_3$Si(CH$_2$)$_3$N$^+$(CH$_3$)$_2$(CH$_2$)$_3$NHSO$_2$(CF$_2$)$_{11}$CF$_3$,
(CH$_3$O)$_3$Si(CH$_2$)$_3$N$^+$(CH$_3$)$_2$(CH$_2$)$_3$NHSO$_2$(CF$_2$)$_{13}$CF$_3$,
(CH$_3$O)$_3$Si(CH$_2$)$_3$N$^+$(CH$_3$)$_2$(CH$_2$)$_3$NHSO$_2$(CF$_2$)$_{15}$CF$_3$,
(CH$_3$O)$_3$Si(CH$_2$)$_3$N$^+$(CH$_3$)$_2$(CH$_2$)$_3$NHSO$_2$(CF$_2$)$_{16}$CF$_3$,
(CH$_3$O)$_3$Si(CH$_2$)$_3$NHC$_6$H$_4$COOH,
(CH$_3$O)$_3$Si(CH$_2$)$_3$NHC$_6$H$_4$COOCH$_3$,
(CH$_3$O)$_3$Si(CH$_2$)$_3$NHC$_6$H$_4$COOC$_2$H$_5$,
(CH$_3$O)$_3$Si(CH$_2$)$_3$NHC$_6$H$_4$COOC$_3$H$_7$,
(CH$_3$O)$_3$Si(CH$_2$)$_3$NHC$_6$H$_4$COOC$_4$H$_9$,
(CH$_3$O)$_3$Si(CH$_2$)$_3$NHC$_6$H$_4$COOCH$_2$C$_6$H$_5$,
(CH$_3$O)$_3$Si(CH$_2$)$_3$NHC$_6$H$_4$COOCH$_2$C$_6$H$_4$NH$_2$,
(CH$_3$O)$_3$Si(CH$_2$)$_3$NHC$_6$H$_4$COOCH$_2$C$_6$H$_4$N(CH$_3$)$_2$,
(CH$_3$O)$_3$Si(CH$_2$)$_3$NHC$_6$H$_4$COOCH$_2$C$_6$H$_4$N(CH$_2$CH$_3$)$_2$,
(CH$_3$O)$_3$Si(CH$_2$)$_3$NHC$_6$H$_4$COOCH$_2$C$_6$H$_4$N(CH$_3$)$_3$Y$^-$,
(CH$_3$O)$_3$Si(CH$_2$)$_3$NHC$_6$H$_4$COOCH$_2$C$_6$H$_4$N$^+$(CH$_2$CH$_3$)$_3$Y$^-$,
(CH$_3$O)$_3$Si(CH$_2$)$_3$NCH$_3$C$_6$H$_4$COOH,
(CH$_3$O)$_3$Si(CH$_2$)$_3$NCH$_3$C$_6$H$_4$COOCH$_3$,
(CH$_3$O)$_3$Si(CH$_2$)$_3$NCH$_3$C$_6$H$_4$COOC$_2$H$_5$,
(CH$_3$O)$_3$Si(CH$_2$)$_3$NCH$_3$C$_6$H$_4$COOC$_3$H$_7$,
(CH$_3$O)$_3$Si(CH$_2$)$_3$NCH$_3$C$_6$H$_4$COOC$_4$H$_9$,
(CH$_3$O)$_3$Si(CH$_2$)$_3$NCH$_3$C$_6$H$_4$COOCH$_2$C$_6$H$_5$,
(CH$_3$O)$_3$Si(CH$_2$)$_3$NCH$_3$C$_6$H$_4$COOCH$_2$C$_6$H$_4$NH$_2$,
(CH$_3$O)$_3$Si(CH$_2$)$_3$NCH$_3$C$_6$H$_4$COOCH$_2$C$_6$H$_4$N(CH$_3$)$_2$,
(CH$_3$O)$_3$Si(CH$_2$)$_3$NCH$_3$C$_6$H$_4$COOCH$_2$C$_6$H$_4$N(CH$_2$CH$_3$)$_2$,
(CH$_3$O)$_3$Si(CH$_2$)$_3$NCH$_3$C$_6$H$_4$COOCH$_2$C$_6$H$_4$N$^+$(CH$_3$)$_3$Y$^-$,
(CH$_3$O)$_3$Si(CH$_2$)$_3$NCH$_3$C$_6$H$_4$COOCH$_2$C$_6$H$_4$N$^+$(CH$_2$CH$_3$)$_3$Y$^-$,
(CH$_3$O)$_3$Si(CH$_2$)$_3$N$^+$(CH$_3$)$_2$C$_6$H$_4$COOHY$^-$,
(CH$_3$O)$_3$Si(CH$_2$)$_3$N$^+$(CH$_3$)$_2$C$_6$H$_4$COOCH$_3$Y$^-$,
(CH$_3$O)$_3$Si(CH$_2$)$_3$N$^+$(CH$_3$)$_2$C$_6$H$_4$COOC$_2$H$_5$Y$^-$,
(CH$_3$O)$_3$Si(CH$_2$)$_3$N$^+$(CH$_3$)$_2$C$_6$H$_4$COOC$_3$H$_7$Y$^-$,
(CH$_3$O)$_3$Si(CH$_2$)$_3$N$^+$(CH$_3$)$_2$C$_6$H$_4$COOC$_4$H$_9$Y$^-$,
(CH$_3$O)$_3$Si(CH$_2$)$_3$N$^+$(CH$_3$)$_2$C$_6$H$_4$COOCH$_2$C$_6$H$_5$Y$^-$,
(CH$_3$O)$_3$Si(CH$_2$)$_3$N$^+$(CH$_3$)$_2$C$_6$H$_4$COOCH$_2$C$_6$H$_4$NH$_2$Y$^-$,
(CH$_3$O)$_3$Si(CH$_2$)$_3$N$^+$(CH$_3$)$_2$C$_6$H$_4$COOCH$_2$C$_6$H$_4$N(CH$_3$)$_2$Y$^-$,
(CH$_3$O)$_3$Si(CH$_2$)$_3$N$^+$(CH$_3$)$_2$C$_6$H$_4$COOCH$_2$C$_6$H$_4$N(CH$_2$CH$_3$)$_2$Y$^-$,
(CH$_3$O)$_3$Si(CH$_2$)$_3$N$^+$(CH$_3$)$_2$C$_6$H$_4$COOCH$_2$C$_6$H$_4$N$^+$(CH$_3$)$_3$Y$^-$Y$^-$,
(CH$_3$O)$_3$Si(CH$_2$)$_3$N$^+$(CH$_3$)$_2$C$_6$H$_4$COOCH$_2$C$_6$H$_4$N$^+$(CH$_2$CH$_3$)$_3$Y$^-$Y$^-$,
(CH$_3$O)$_3$Si(CH$_2$)$_3$NC$_2$H$_5$C$_6$H$_4$COOH,
(CH$_3$O)$_3$Si(CH$_2$)$_3$NC$_2$H$_5$C$_6$H$_4$COOCH$_3$,
(CH$_3$O)$_3$Si(CH$_2$)$_3$NC$_2$H$_5$C$_6$H$_4$COOC$_3$H$_7$,
(CH$_3$O)$_3$Si(CH$_2$)$_3$NC$_2$H$_5$C$_6$H$_4$COOC$_4$H$_9$,
(CH$_3$O)$_3$Si(CH$_2$)$_3$NC$_2$H$_5$C$_6$H$_4$COOCH$_2$C$_6$H$_5$,
(CH$_3$O)$_3$Si(CH$_2$)$_3$NC$_2$H$_5$C$_6$H$_4$COOCH$_2$C$_6$H$_4$NH$_2$,
(CH$_3$O)$_3$Si(CH$_2$)$_3$NC$_2$H$_5$C$_6$H$_4$COOCH$_2$C$_6$H$_4$N(CH$_3$)$_2$,
(CH$_3$O)$_3$Si(CH$_2$)$_3$NC$_2$H$_5$C$_6$H$_4$COOCH$_2$C$_6$H$_4$N(CH$_2$CH$_3$)$_2$,
(CH$_3$O)$_3$Si(CH$_2$)$_3$NC$_2$H$_5$C$_6$H$_4$COOCH$_2$C$_6$H$_4$N$^+$(CH$_3$)$_3$Y$^-$,
(CH$_3$O)$_3$Si(CH$_2$)$_3$NC$_2$H$_5$C$_6$H$_4$COOCH$_2$C$_6$H$_4$N$^+$(CH$_2$CH$_3$)$_3$Y$^-$,
(CH$_3$O)$_3$Si(CH$_2$)$_3$N$^+$(C$_2$H$_5$)$_2$C$_6$H$_4$COOHY$^-$,
(CH$_3$O)$_3$Si(CH$_2$)$_3$N$^+$(C$_2$H$_5$)$_2$C$_6$H$_4$COOCH$_3$Y$^-$,
(CH$_3$O)$_3$Si(CH$_2$)$_3$N$^+$(C$_2$H$_5$)$_2$C$_6$H$_4$COOC$_2$H$_5$Y$^-$,
(CH$_3$O)$_3$Si(CH$_2$)$_3$N$^+$(C$_2$H$_5$)$_2$C$_6$H$_4$COOC$_3$H$_7$Y$^-$,
(CH$_3$O)$_3$Si(CH$_2$)$_3$N$^+$(C$_2$H$_5$)$_2$C$_6$H$_4$COOC$_4$H$_9$Y$^-$,
(CH$_3$O)$_3$Si(CH$_2$)$_3$N$^+$(C$_2$H$_5$)$_2$C$_6$H$_4$COOCH$_2$C$_6$H$_5$Y$^-$,
(CH$_3$O)$_3$Si(CH$_2$)$_3$N$^+$(C$_2$H$_5$)$_2$C$_6$H$_4$COOCH$_2$C$_6$H$_4$N$_2$Y$^-$,
(CH$_3$O)$_3$Si(CH$_2$)$_3$N$^+$(C$_2$H$_5$)$_2$C$_6$H$_4$COOCH$_2$C$_6$H$_4$N(CH$_3$)$_2$Y$^-$,
(CH$_3$O)$_3$Si(CH$_2$)$_3$N$^+$(CH$_3$)$_2$C$_6$H$_4$COOCH$_3$Y$^-$,
(CH$_3$O)$_3$Si(CH$_2$)$_3$N$^+$(CH$_3$)$_2$C$_6$H$_4$COOC$_2$H$_5$Y$^-$,
(CH$_3$O)$_3$Si(CH$_2$)$_3$N$^+$(CH$_3$)$_2$C$_6$H$_4$COOC$_3$H$_7$Y$^-$,
(CH$_3$O)$_3$Si(CH$_2$)$_3$N$^+$(CH$_3$)$_2$C$_6$H$_4$COOC$_4$H$_9$Y$^-$,
(CH$_3$O)$_3$Si(CH$_2$)$_3$N$^+$(CH$_3$)$_2$C$_6$H$_4$COOCH$_2$C$_6$H$_5$Y$^-$,
(CH$_3$O)$_3$Si(CH$_2$)$_3$N$^+$(CH$_3$)$_2$C$_6$H$_4$COOCH$_2$C$_6$H$_4$NH$_2$Y$^-$,
(CH$_3$O)$_3$Si(CH$_2$)$_3$N$^+$(CH$_3$)$_2$C$_6$H$_4$COOCH$_2$C$_6$H$_4$N(CH$_3$)$_2$Y$^-$, (CH₃O)₃Si(CH₂)₃N⁺(CH₃)₂C₆H₄COOCH₂C₆H₄N(CH₂CH₃)₂Y⁻,
(CH₃O)₃Si(CH₂)₃N⁺(CH₃)₂C₆H₄COOCH₂C₆H₄N⁺(CH₃)₃Y⁻Y⁻,
(CH₃O)₃Si(CH₂)₃N⁺(CH₃)₂C₆H₄COOCH₂C₆H₄N⁺(CH₂CH₃)₃Y⁻Y⁻
(CH₃O)₃Si(CH₂)₃NC₂H₅C₆H₄COOH,
(CH₃O)₃Si(CH₂)₃NC₂H₅C₆H₄COOCH₃,
(CH₃O)₃Si(CH₂)₃NC₂H₅C₆H₄COOC₃H₇,
(CH₃O)₃Si(CH₂)₃NC₂H₅C₆H₄COOC₄H₉,
(CH₃O)₃Si(CH₂)₃NC₂H₅C₆H₄COOCH₂C₆H₅,
(CH₃O)₃Si(CH₂)₃NC₂H₅C₆H₄COOCH₂C₆H₄NH₂,
(CH₃O)₃Si(CH₂)₃NC₂H₅C₆H₄COOCH₂C₆H₄N(CH₃)₂,
(CH₃O)₃Si(CH₂)₃NC₂H₅C₆H₄COOCH₂C₆H₄N(CH₂CH₃)₂,
(CH₃O)₃Si(CH₂)₃NC₂H₅C₆H₄COOCH₂C₆H₄N⁺(CH₃)₃Y⁻,
(CH₃O)₃Si(CH₂)₃NC₂H₅C₆H₄COOCH₂C₆H₄N⁺(CH₂CH₃)₃Y⁻,
(CH₃O)₃Si(CH₂)₃N⁺(C₂H₅)₂C₆H₄COOHY⁻,
(CH₃O)₃Si(CH₂)₃N⁺(C₂H₅)₂C₆H₄COOCH₃Y⁻,
(CH₃O)₃Si(CH₂)₃N⁺(C₂H₅)₂C₆H₄COOC₂H₅Y⁻,
(CH₃O)₃Si(CH₂)₃N⁺(C₂H₅)₂C₆H₄COOC₃H₇Y⁻,
(CH₃O)₃Si(CH₂)₃N⁺(C₂H₅)₂C₆H₄COOC₄H₉Y⁻,
(CH₃O)₃Si(CH₂)₃N⁺(C₂H₅)₂C₆H₄COOCH₂C₆H₅Y⁻,
(CH₃O)₃Si(CH₂)₃N⁺(C₂H₅)₂C₆H₄COOCH₂C₆H₄N₂Y⁻,
(CH₃O)₃Si(CH₂)₃N⁺(C₂H₅)₂C₆H₄COOCH₂C₆H₄N(CH₃)₂Y⁻,
(CH₃CH₂O)₃Si(CH₂)₃N⁺(CH₃)₂C₆H₄COOC₃H₇Y⁻,
(CH₃CH₂O)₃Si(CH₂)₃N⁺(CH₃)₂C₆H₄COOC₄H₉Y⁻,
(CH₃CH₂O)₃Si(CH₂)₃N⁺(CH₃)₂C₆H₄COOCH₂C₆H₅Y⁻,
(CH₃CH₂O)₃Si(CH₂)₃N⁺(CH₃)₂C₆H₄COOCH₂C₆H₄NH₂Y⁻,
(CH₃CH₂O)₃Si(CH₂)₃N⁺(CH₃)₂C₆H₄COOCH₂C₆H₄N(CH₃)₂Y⁻,
(CH₃CH₂O)₃Si(CH₂)₃N⁺(CH₃)₂C₆H₄COOCH₂C₆H₄N(CH₂CH₃)₂Y⁻,
(CH₃CH₂O)₃Si(CH₂)₃N⁺(CH₃)₂C₆H₄COOCH₂C₆H₄N⁺(CH₃)₃Y⁻Y⁻,
(CH₃CH₂O)₃Si(CH₂)₃N⁺(CH₃)₂C₆H₄COOCH₂C₆H₄N⁺(CH₂CH₃)₃Y⁻Y⁻,
(CH₃CH₂O)₃Si(CH₂)₃NC₂H₅C₆H₄COOH,
(CH₃CH₂O)₃Si(CH₂)₃NC₂H₅C₆H₄COOCH₃,
(CH₃CH₂O)₃Si(CH₂)₃NC₂H₅C₆H₄COOC₂H₅,
(CH₃CH₂O)₃Si(CH₂)₃NC₂H₅C₆H₄COOC₃H₇,
(CH₃CH₂O)₃Si(CH₂)₃NC₂H₅C₆H₄COOC₄H₉,
(CH₃CH₂O)₃Si(CH₂)₃NC₂H₅C₆H₄COOCH₂C₆H₅,
(CH₃CH₂O)₃Si(CH₂)₃NC₂H₅C₆H₄COOCH₂C₆H₄NH₂,
(CH₃CH₂O)₃Si(CH₂)₃NC₂H₅C₆H₄COOCH₂C₆H₄N(CH₃)₂,
(CH₃CH₂O)₃Si(CH₂)₃NC₂H₅C₆H₄COOCH₂C₆H₄N(CH₂CH₃)₂,
(CH₃CH₂O)₃Si(CH₂)₃NC₂H₅C₆H₄COOCH₂C₆H₄N⁺(CH₃)₃Y⁻,
(CH₃CH₂O)₃Si(CH₂)₃NC₂H₅C₆H₄COOCH₂C₆H₄N⁺(CH₂CH₃)₃Y⁻,
(CH₃CH₂O)₃Si(CH₂)₃N⁺(C₂H₄)₂C₆H₄COOHY⁻,
(CH₃CH₂O)₃Si(CH₂)₃N⁺(C₂H)₂C₆H₄COOCH₃Y⁻,
(CH₃CH₂O)₃Si(CH₂)₃N⁺(C₂H₅)₂C₆H₄COOC₂H₅Y⁻,
(CH₃CH₂O)₃Si(CH₂)₃N⁺(C₂H₅)₂C₆H₄COOC₃H₇Y⁻,
CH₃CH₂O)₃Si(CH₂)₃N⁺(C₂H₅)₂C₆H₄COOC₄H₉Y⁻,
(CH₃CH₂O)₃Si(CH₂)₃N⁺(C₂H₅)₂C₆H₄COOCH₂C₆H₅Y⁻,
(CH₃CH₂O)₃Si(CH₂)₃N⁺(C₂H₅)₂C₆H₄COOCH₂C₆H₄NH₂Y⁻,
(CH₃CH₂O)₃Si(CH₂)₃N⁺(C₂H₅)₂C₆H₄COOCH₂C₆H₄N(CH₃)₂Y⁻,
(CH₃CH₂O)₃Si(CH₂)₃N⁺(C₂H₂C₆H₄COOCH₂C₆H₄N(CH₂CH₂Y⁻,
(CH₃CH₂O)₃Si(CH₂)₃N⁺(C₂H₅)₂C₆H₄N⁺(CH₃)₃Y⁻Y⁻, or
(CH₃CH₂O)₃Si(CH₂)₃N⁺(C₂H₅)₂C₆H₄N⁺CH₂CH₃Y⁻Y⁻.

4. The composition of claim 1 formed from mixing an organosilane of the formula II, III, IV, or V:

$$(R_1)_3SiR_2N^+(R_3)(R_4)(R_5)Y^- \quad (II)$$

$$(R_1)_3SiR_2N(R_3)(R_4) \quad (III)$$

$$(R_1)_3SiR_2R_{35} \quad (IV)$$

$$(R_1)_2Si(R_{36})(R_{37}) \quad (V)$$

wherein each $R_1$ is, independently, halogen or $R_6O$, where $R_6$ is H, alkyl of from 1 to about 22 carbon atoms, acetyl, acetoxy, acyl, propylene glycol, ethylene glycol, polyethylene glycol, polypropylene glycol; block and copolymers of ethylene and propylene glycol, the alkyl monoether of from 1 to 22 carbons of propylene glycol, ethylene glycol, polyethylene glycol, polypropylene glycol; block and copolymers of ethylene and propylene glycol or the monoester of a carbonic acid of from 1 to 22 carbons and propylene glycol, ethylene glycol, polyethylene glycol, polypropylene glycol; block and copolymers of ethylene and propylene glycol; octyphenol; nonylphenol; or sorbitan ethers;

$R_{35}$ is H, halogen, $NH_2(CH_2)_2NH$, $NH_2$, $C_3H_5O_2$, $C_4H_5O_2$, $NaO(CH_3O)P(O)$, or $ClCH_2C_6H_4$;

$R_{36}$ and $R_{37}$ are, independently, halogen, H, alkyl of from 1 to about 8 carbon atoms, acrylic, vinyl, acetylenic, benzyl, styryl, propinyl, isobutyl, phenyl, or n-octyl;

$R_2$ is benzyl, vinyl or alkyl of from 1 to about 22 carbon atoms;

$R_3$ and $R_4$ are, independently, lower alkyl alcohol, lower alkoxy of from 1 to 4 carbon atoms, alkyl of from 1 to about 22 carbon atoms; or $R_3$ and $R_4$ can, together, form a morpholine or cyclic or heterocyclic, unsaturated or saturated, five to seven-membered ring of the formula VI:

$$—R_3—(R_7)_k—R_4— \quad (VI)$$

where k is an integer from 0 to 2, $R_7$, where the ring is saturated, is $CH_2$, O, S, NH, $NH_2^+$, $NCH_2CH_2NH_2$, $NCH_2CH_2NH_3^+$, $NCH_2CH_2N(R_8)(R_9)$, $NCH_2CH_2N^+(R_8)(R_9)(R_{10})$, N(alkyl), N(aryl), N(benzyl), where each $R_8$, $R_9$, and $R_{10}$ is, independently, benzyl, polyether, lower alkyl alcohol of from 1 to 4 carbon atoms, lower alkoxy of from 1 to 4 carbon atoms, or alkyl of from 1 to about 22 carbon atoms, and $R_7$, where the ring is unsaturated is, CH, N, N⁺H, N⁺(alkyl), N⁺(aryl), N⁺(benzyl), N—CH₂—N, N⁺H—CH₂—N, N⁺(alkyl)-CH₂—N, N⁺(aryl)-CH₂—N, or N⁺(benzyl)-CH₂—N; wherein the ring is unsubstituted or substituted with alkyl of from 1 to 22 carbon atoms, ester, aldehyde, carboxylate, amide, thionamide, nitro, amine, or halide $R_5$ is lower alkyl alcohol, $CH_2C_6H_5$, polyether, alkyl, alkoxy, perfluoroalkyl, pefluoroalkylsulfonate, or perfluoroalkylcarboxylate wherein the alkyl, alkoxy, perfluoroalkyl, pefluoroalkylsulfonate, or perfluoroalkylcarboxylate is from 1 to about 22 carbon atoms or is a five to seven-membered ring according to formula VI as described above; and $Y^-$ is a suitable anionic moiety to form the salt of the compound of formula II, III, IV or V, with a polyol containing at least two hydroxy groups, wherein any of the at least two hydroxy groups are separated by no more than two intervening atoms.

5. The composition of claim 1, wherein the organosilane is 3-(trimethoxysilyl) propyldimethyloctadecyl ammonium chloride, 3-(trimethoxysily)propylmethyldi(decyl) ammonium chloride, 3-chloropropyl trimethoxysilane, 3-chloropropyltrimethoxysilane, octadecyltrimethoxysilane, or perfluorooctyltriethoxysilane.

6. A method of treating a substrate, comprising contacting the substrate with a sufficient amount of the composition of claim 1 for a period of time sufficient for treatment of the substrate.

* * * * *